United States Patent
Gandelman et al.

(10) Patent No.: US 10,399,917 B2
(45) Date of Patent: Sep. 3, 2019

(54) PROCESS FOR THE PREPARATION OF ORGANIC BROMIDES

(71) Applicant: Technion Research & Development Foundation Limited, Haifa (IL)

(72) Inventors: Mark Gandelman, Kfar-Sava (IL); Gennady Nisnevich, Haifa (IL); Kseniya Kulbitski, Haifa (IL); Alexander Artaryan, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 15/763,846

(22) PCT Filed: Oct. 6, 2016

(86) PCT No.: PCT/IL2016/051083
§ 371 (c)(1),
(2) Date: Mar. 28, 2018

(87) PCT Pub. No.: WO2017/060905
PCT Pub. Date: Apr. 13, 2017

(65) Prior Publication Data
US 2018/0273450 A1    Sep. 27, 2018

Related U.S. Application Data

(60) Provisional application No. 62/238,197, filed on Oct. 7, 2015.

(51) Int. Cl.
| | | |
|---|---|---|
| C07C 17/363 | (2006.01) |
| C07C 19/075 | (2006.01) |
| C07C 23/10 | (2006.01) |
| C07C 25/02 | (2006.01) |
| C07C 67/32 | (2006.01) |
| C07C 41/22 | (2006.01) |
| C07C 201/12 | (2006.01) |
| C07B 39/00 | (2006.01) |
| C07C 45/67 | (2006.01) |
| C07D 205/04 | (2006.01) |
| C07C 253/30 | (2006.01) |
| C07D 209/48 | (2006.01) |
| C07D 211/38 | (2006.01) |
| C07J 9/00 | (2006.01) |
| C07C 255/65 | (2006.01) |
| C07C 409/34 | (2006.01) |

(52) U.S. Cl.
CPC ............ *C07C 17/363* (2013.01); *C07B 39/00* (2013.01); *C07C 19/075* (2013.01); *C07C 23/10* (2013.01); *C07C 25/02* (2013.01); *C07C 41/22* (2013.01); *C07C 45/676* (2013.01); *C07C 67/32* (2013.01); *C07C 201/12* (2013.01); *C07C 253/30* (2013.01); *C07D 205/04* (2013.01); *C07D 209/48* (2013.01); *C07D 211/38* (2013.01); *C07J 9/005* (2013.01); *C07C 255/65* (2013.01); *C07C 409/34* (2013.01); *C07C 2601/04* (2017.05); *C07C 2601/14* (2017.05); *C07C 2602/42* (2017.05); *C07C 2603/74* (2017.05); *C07C 2603/90* (2017.05)

(58) Field of Classification Search
CPC .................................................. C07C 17/363
See application file for complete search history.

(56) References Cited

FOREIGN PATENT DOCUMENTS

| | | |
|---|---|---|
| IN | IN803DEL1999 | 6/2005 |
| WO | WO 2011154953 A1 | 12/2011 |

OTHER PUBLICATIONS

Sodré (Sodré, L. R. et al. "A Green Hunsdiecker Reaction of Cinnamic Acids" J. Braz. Chem. Soc., vol. 24, No. 2, 2013) (Year: 2013).*
Derek H.R. Barton et al. "The invention of new radical chain reactions. Part VIII. Radical chemistry of thiohydroxamic esters; A new method for the generation of carbon radicals from carboxylic acids" Barton et al., Tetrahedron vol. 41, Issue 19, 1985, pp. 3901-3924.
Derek H.R. Barton et al., The invention of radical reactions: Part XVI. Radical decarboxylative bromination and iodination of aromatic acids, Tetrahedron, vol. 43, Issue 19, 1987, pp. 4321-4328.
D. Naskar; et al., "1-Haloalkynes from Propiolic Acids: A Novel Catalytic Halodecarboxylation Protocol", Journal of Organic Chemistry, (19991008), vol. 64, ISSN 0022-3263, pp. 6896-6897, XP 002656405 [A].
D. Naskar; et al., "Catalytic Hunsdiecker Reaction and One-Pot Catalytic Hunsdiecker-Heck Strategy: Synthesis of alpha,beta-Unsaturated Aromatic Halides, alpha-(Dihalomethyl) benzenemethanols, 5-Aryl-2,4-pentadienoic acids, Dienoates and Dienamides", Tetrahdron, (20000000), vol. 56, ISSN 0040-4020, pp. 1369-1377, XP 002656408 [A].
F.G. Bordwell et al., "Synthesis of Dihalomethyl and alpha-Haloalkyl Sulfones by the Halogenative Decarboxylation of alpha-Aryl- and alpha-Alkylsulfonylakanecarboxylic Acids", Journal of Organic Chemistry, (19740101), vol. 39, ISSN 0022-3263, pp. 2516-2519, XP055521306 [A].
Hiromi Hamamoto et al., Hypervalent Iodine(III)-LiX Combination in Fluoroalcohol Solvent for Aromatic Halogenation of Electron-Rich Arenecarboxylic Acids Synlett 2011(11): 1563-1566.
International Search Report for PCT application No. PCT/IL2016/051083, dated Oct. 6, 2016.
International Search Report for PCT application No. PCT/IL2016/051084, dated Dec. 21, 2016.
Jaya Prakash Das, and Sujit Roy,"Catalysynthetic Hunsdiecker Reaction of α,β-Unsaturated Carboxylic Acids: How Efficient Is the Catalyst?", J. Org. Chem., 2002, 67 (22), pp. 7861-7864.

(Continued)

*Primary Examiner* — Medhanit W Bahta
(74) *Attorney, Agent, or Firm* — Cheryl J. Schindler; Pearl Cohen Zedek Latzer Baratz LLP

(57) ABSTRACT

The present invention provides a process for the preparation of organic bromides, by a radical bromodecarboxylation of carboxylic acids with a bromoisocyanurate.

36 Claims, No Drawings

(56) References Cited

OTHER PUBLICATIONS

John A. Davis, et al., "Modifications of the Hunsdiecker Reaction", J. Org. hem., 1965, 30 (2), pp. 415-417.
J. Braz. Chem. Soc. "Oxidative Dehydration of Glycerol to Acrylic Acid over Vanadium-Impregnated Zeolite Beta", 2013, v. 24, 213.
Kristin Janz and Neelu Kaila, Bromodecarboxylation of Quinoline Salicylic Acids: Increasing the Diversity of Accessible Substituted Quinolines, J. Org. Chem., 2009, 74 (22), pp. 8874-8877.
Leonardo S. de Almeida et al., "Tribromoisocyanuric Acid in Trifluoroacetic Acid: An Efficient System for Smooth Brominating of Moderately Deactivated Arenes", Synlett 2013 v. 24, 603-606.
Leonardo R. Sodre et al. "A Green Hunsdiecker Reaction of Cinnamic Acids", Journal of Brazilian Chemical Society, vol. 24, No. 2, Jan. 2013, pp. 212-218, XP55572808.
Martin Brzozowski et al., Synthesis of substituted 4-(1H-indol-6-yl)-1H-indazoles as potential PDK1 inhibitors,Tetrahedron vol. 70, Issue 2, Jan. 18, 2014, pp. 318-326.
W Gottardi—Monatshefte fur Chemie Chemical Monthly, 1968, v. 99, pp. 815-822.
N.J. Bunce and N.G. Murray, "On the relationship between the Hunsdiecker and Simonini reactions", Tetrahedron 1971, v. 27, 5323-5335.
Pelayo Camps et al., "Hunsdiecker-Type Bromodecarboxylation of Carboxylic Acids with Iodosobenzene Diacetate-Bromine", Tetrahedron 2000, v. 56, 2703-2707.
Randy W.Jackson et al., The discovery and structure-activity relationships of pyrano[3,4-b]indole-based inhibitors of hepatitis C virus NS5B polymerase, Bioorg. Med. Chem. Lett. 2011, v. 21, 3227-3231.
S. Chowdhury; et al., "The First Example of a Catalytic Hunsdiecker Reaction: Synthesis of beta-Halostyrenes", Journal of Organic Chemistry, (19770101), vol. 62, ISSN 0022-3263, pp. 199-200, XP 002656406 [A].
Supplementary European Search Report for EP 16853205 dated Mar. 22, 2019.
Supplementary European Search Report for EP 16853206 dated Apr. 9, 2019.
Yong Luo et al., "Silver-catalyzed decarboxylative halogenation of carboxylic acids", Tetrahedron Letters 2010, vol. 51, Issue 50, Dec. 15, 2010, pp. 6646-6648.
Zejiang Li, Kunkai Wang, Zhong-Quan Liu, "Transition-Metal-Free Hunsdiecker Reaction of Electron-Rich Arenecarboxylic Acids and Aryl Aldehydes in Water", Synlett 2014; 25(17): 2508-2512.

* cited by examiner

PROCESS FOR THE PREPARATION OF ORGANIC BROMIDES

CROSS-REFERENCE TO RELATED APPLICATIONS

This application is a National Phase Application of PCT International Application No. PCT/IL2016/051083, International Filing Date Oct. 6, 2016, claiming priority of U.S. Provisional Patent Application No. 62/238,197, filed Oct. 7, 2015, which are hereby incorporated by reference.

FIELD OF THE INVENTION

The present invention provides a process for the preparation of organic bromides, by a radical bromodecarboxylation of carboxylic acids with a bromoisocyanurate. The invention further provides a radiation sensitive composition comprising a carboxylic acid and bromoisocyanurate which generates organic bromide upon electromagnetic irradiation.

BACKGROUND OF THE INVENTION

Organic bromides are stable organic compounds, which are used commercially for many applications, such as pharmaceuticals, agriculture, disinfectants, flame extinguishing agents, and dyes. Organic bromides have found wide use in numerous industrial applications as chemical intermediates for the production of other commercial organic compounds (*Ullmann's Encyclopedia of Industrial Chemistry* 2012, v. 6, 331-358; v. 8, 483-519).

Reaction of benzoic acid with tribromoisocyanuric acid (TBCA) in trifluoroacetic acid gave only 3-bromobenzoic acid—the product of electrophilic bromination of aromatic C—H bond (*Synlett* 2013 v. 24, 603-605).

Organic carboxylic acids are widely available and cheap raw materials in organic synthesis. Therefore, the oxidative decarboxylation of organic carboxylic acids with concomitant replacement by bromine (bromodecarboxylation) is an extremely useful method for regioselective synthesis of organic bromides.

The Hunsdiecker reaction (*Tetrahedron* 1971, v. 27, 5323) is a bromodecarboxylation reaction, which utilizes the treatment of anhydrous silver salt of organic acid with molecular bromine in an inert solvent. This reaction, however, is extremely sensitive to presence of trace amounts of water, which lead to the recovery of unreacted acid. Another way to perform the Hunsdiecker reaction is by using a mixture of organic carboxylic acid and $Br_2/HgO$ (*J. Org. Chem.* 1965, v. 30, 415) instead of the silver salt.

Accordingly, the Hunsdiecker reaction and/or its modifications use heavy metal salts such as those of silver and mercury, therefore the disadvantages of such procedures for the pharmaceutical industry are obvious.

The Barton halo-de-carboxylation procedure (Barton et al., *Tetrahedron* 1985, v. 41, 3901; 1987, v. 43, 4321) is directed to the conversion of organic carboxylic acids to the esters of N-hydroxypyridine-2-thione. The thiohydroxamic esters are brominated by $BrCCl_3$. Thiopyridines are formed in the reaction as co-products.

Additional process for converting organic carboxylic acids to their corresponding bromides is by treating the carboxylic acid with (diacetoxyiodo)benzene and bromine or LiBr as bromine source (*Tetrahedron* 2000, v. 56, 2703; *Synlett* 2011, 1563). However, in this reaction, it is difficult to separate the desired product from iodobenzene, which is formed as co-product in the reaction.

A bromodecarboxylation of aromatic carboxylic acids using $CuBr_2$ as the halogen sources has been developed by Wu et. al. (*Tetrahedron Letters* 2010, v. 51, 6646) and Liu et. al. (*Tetrahedron Letters* 2013, v. 54, 3079), which also utilize the use of heavy metals in their reactions.

Another example for bromodecarboxylation utilizes the reagent system 1205-KBr for bromodecarboxylation of electron-rich arenecarboxylic acids (*Synlett* 2014, v. 25, 2508). This method, however, is limited to preparation of specific brominated phenol ether derivatives.

N-Bromoamides such as N-bromosuccinimide (*Chem. Pharm. Bull.* 2002, v. 50, 941), 1,3-dibromo-5,5-dimethylhydantoin (*Bioorg. Med. Chem.* 2008, v. 16, 10001; *Bioorg. Med. Chem. Lett.* 2011, v. 21, 3227; *Tetrahedron* 2014, v. 70, 318), dibromoisocyanuric acid (*Monatsh. Chem.* 1968, v. 99, 815; 1969, v. 100, 42 & 1977, v. 108, 1067), tribromoisocyanuric acid (*Synlett* 2013, v. 24, 603), are useful reagents for the electrophilic bromination of aromatic carboxylic acids in the meta-position with respect to the carboxylic group. However, the use of these reagents in bromo-decarboxylation reactions is rather limited.

For example, reaction of N-bromosuccinimide with arenecarboxylic acids, predominantly electron-rich arenecarboxylic acids, yields bromoarenes (IN803DEL1999; JOC 2009, v. 74, 8874; *Tetrahedron Lett.* 2007, v. 48, 5429). Reaction of 3-aryl acrylic and propiolic acids with N-bromosuccinimides (*J. Org. Chem.* 2002, v. 67, 7861) and tribromoisocyanuric acid (*J. Braz. Chem. Soc.* 2013, v. 24, 213) yields 2-bromovinyl and 2-bromoethynyl arenes. All of these reactions are heterolytic reactions that do not require initiation with radical initiators or UV-visible light irradiation.

The conversion of carboxylic acid $R—CO_2H$, to their corresponding bromide, R—Br, is therefore a rather difficult transformation. There is a need for the development of new strategies for bromodecarboxylation.

SUMMARY OF THE INVENTION

In one embodiment, this invention is directed to a process for the preparation of organic bromide of formula (1A) from a carboxylic acid of formula (2A) represented by scheme 1:

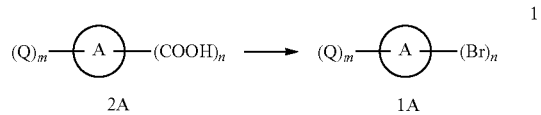

said process comprises radical bromodecarboxylation reaction of carboxylic acid (2A) with a bromoisocyanurate to yield organic bromide (1A);
wherein
said bromoisocyanurate is tribromoisocyanuric acid, dibromoisocyanuric acid, bromodichloroisocyanuric acid, dibromochloroisocyanuric acid, bromochloroisocyanuric acid, or any combination thereof;
A is arene, alkane, cycloalkane or saturated heterocycle;
n is an integer of at least 1;
m is an integer of at least 0; and
each Q is independently F, Cl, Br, $R^1$, acyl, $C(O)R^1$, $C(O)OR^1$, C(O)OMe, C(O)Cl, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;

wherein each $R^1$ is independently aryl, alkyl, cycloalkyl or heterocyclyl, wherein said $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $R^2$ in (2A) is carboxylic group COOH, then the respective $R^2$ in (1A) is Br;

wherein the position of said Br and Q in said structure of formula (1A) correspond to the same position of said COOH and Q, respectively in said structure of formula (2A).

In one embodiment, this invention is directed to a process for the preparation of bromoarene (1B)

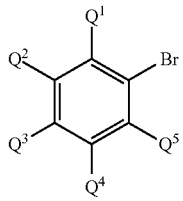

from an arenecarboxylic acid (2B),

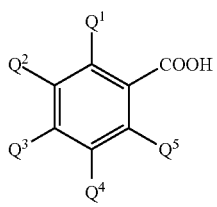

wherein said process comprises radical bromodecarboxylation reaction of carboxylic acid (2B) with a bromoisocyanurate;

wherein $Q^1$, $Q^2$, $Q^3$, $Q^4$, and $Q^5$, are each independently selected from: H, F, Cl, Br, $R^1$, COOH, acyl, $C(O)R^1$, $C(O)OR^1$, C(O)OMe, C(O)Cl, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^2$, $N(R^1)SO_2R^1$, $N(acyl)_2$, $N[C(O)R^1]SO_2R^1$, $N[C(O)R^1]_2$, $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;

wherein each $R^1$ is independently aryl, alkyl, cycloalkyl or heterocyclyl; wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Br.

In one embodiment, this invention is directed to a radiation-sensitive composition comprising carboxylic acid of formula (2A)

and bromoisocyanurate which generates organic bromide of formula (1A)

upon electromagnetic irradiation, wherein the bromoisocyanurate is tribromoisocyanuric acid, dibromoisocyanuric acid, bromodichloroisocyanuric acid, dibromochloroisocyanuric acid, bromochloroisocyanuric acid, or any combination thereof;

A is arene, alkane, cycloalkane or saturated heterocycle;

n is an integer of at least 1;

m is an integer of at least 0;

each Q is independently F, Cl, Br, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;

wherein each $R^1$ is independently aryl, alkyl, cycloalkyl or heterocyclyl, wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $R^2$ in (2A) is a carboxylic group COOH, then the respective $R^2$ in (1A) is Br;

wherein the position of said Br and Q in said structure of formula (1A) correspond to the same position of said COOH and Q, respectively in said structure of formula (2A).

In one embodiment, this invention is directed to a composition comprising an organic bromide of formula (1A) or (1B)

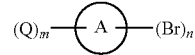

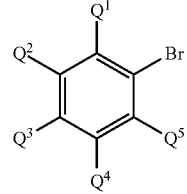

wherein said organic bromide of formula (1A) or (1B) is prepared according to the process of this invention.

In one embodiment, the process and composition of this invention further comprises an additive. In another embodiment, said additive is $Br_2$ (bromine), a salt comprising bromide or a polybromide anion and an organic or inorganic cation; or any combination thereof.

In one embodiment, the process of the invention is conducted in the presence of an organic or an inorganic solvent or combination thereof and the composition of this invention comprises an organic or inorganic solvent or combination thereof. In another embodiment, the inorganic solvent is $CO_2$ or $SO_2$, or combination thereof. In another embodiment, the organic solvent is $CH_3CN$, $CH_3NO_2$, an ester, a hydrocarbon solvent, or halocarbon solvent or combination thereof. In another embodiment, the hydrocarbon solvent is $C_6H_6$. In another embodiment, the halocarbon solvent is $CH_2Cl_2$, $Cl(CH_2)_2Cl$, $CHCl_3$, $CCl_4$, $C_6H_5Cl$, o-$C_6H_4Cl_2$, $BrCCl_3$, $CH_2Br_2$, $CFCl_3$, $CF_3CCl_3$, $ClCF_2CFCl_2$, $BrCF_2CFClBr$, $CF_3CClBr_2$, $CF_3CHBrCl$, $C_6H_5F$, $C_6H_5CF_3$, 4-$ClC_6H_4CF_3$, 2,4-$Cl_2C_6H_3CF_3$ or any combination thereof.

In one embodiment, in order to accelerate the radical bromodecarboxylation reaction the reaction mixture is subjected to electromagnetic irradiation. In another embodiment, the electromagnetic irradiation is microwave, infrared, ultraviolet, or visible light irradiation or any combination thereof. In another embodiment, the electromagnetic irradiation is visible light irradiation. In another embodiment, the source of said visible light is sunlight, fluorescent lamp, light-emitting diode, incandescent lamp or any combination thereof.

In one embodiment, the process and composition of this invention comprises bromoisocyanurate and a carboxylic acid compound of formula (2A) or (2B). In another embodiment, the molar ratio between bromoisocyanurate/(each carboxylic group of the carboxylic acid of formula (2A)) is between 0.1 and 2.

In one embodiment, the process and composition of this invention comprises bromoisocyanurate, additive and a carboxylic acid compound of formula (2A) or (2B). In another embodiment, the molar ratio between the additive/(each carboxylic group of the carboxylic acid of formula (2A)) is between 0.1 and 4.

In one embodiment, the bromodecarboxylation reaction is conducted at a temperature of between −20° C. and 150° C. In another embodiment, the bromodecarboxylation reaction is conducted at a temperature of between 0° C. and 100° C.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In recent years, free radical reactions have developed greatly in the general field of organic synthesis. These free radical reactions have a number of significant advantages relative to the more conventional ionic reactions. First, free radical chain reactions can generally be conducted under neutral conditions. In addition, these reactions are performed under very mild conditions, which make it possible to avoid interference of a steric or polar nature occurring with the starting materials. Furthermore, this type of reaction is generally not accompanied by spurious reactions of carbocationic rearrangement or carbanionic elimination.

The present invention therefore had the object of perfecting a new process for the formation of carbon containing free radicals, the functionality of which is unmodified relative to the starting materials. The process of the invention consists essentially of a free radical bromodecarboxylation of organic acids which can be aromatic or aliphatic carboxylic acid. The mild conditions for carrying out this process have enabled excellent yields of free radicals to be obtained which retain, in particular, the ether, ester, ketone, and nitro functions of the starting material.

In one embodiment, this invention is directed to a process for the preparation of organic bromide of formula (1A) from a carboxylic acid of formula (2A) represented by scheme 1:

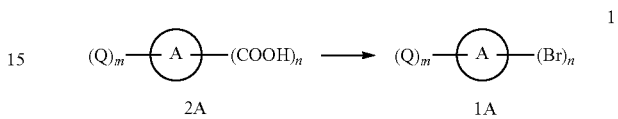

said process comprises radical bromodecarboxylation reaction of carboxylic acid (2A) with a bromoisocyanurate to yield organic bromide (1A);
wherein
said bromoisocyanurate is tribromoisocyanuric acid, dibromoisocyanuric acid, bromodichloroisocyanuric acid, dibromochloroisocyanuric acid, bromochloroisocyanuric acid, or any combination thereof;
A is arene, alkane, cycloalkane or saturated heterocycle;
n is an integer of at least 1;
m is an integer of at least 0; and
each Q is independently F, Cl, Br, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;
wherein each $R^1$ is independently aryl, alkyl, cycloalkyl or heterocyclyl, wherein said $R^1$ is optionally substituted by one or more substituents of $R^2$;
wherein each $R^2$ is independently F, Cl, Br, COOH, acyl, aryl, alkyl, cycloalkyl or heterocyclyl;
wherein if either one of $R^2$ in (2A) is carboxylic group COOH, then the respective $R^2$ in (1A) is Br;
wherein the position of said Br and Q in said structure of formula (1A) correspond to the same position of said COOH and Q, respectively in said structure of formula (2A).

In one embodiment, this invention is directed to a process for the preparation of organic bromide of formula (1B) from a carboxylic acid of formula (2B) represented by scheme 2:

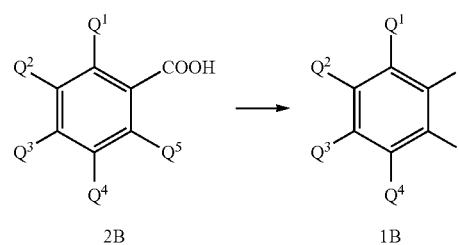

said process comprises radical bromodecarboxylation reaction of carboxylic acid (2B) with a bromoisocyanurate to yield organic bromide (1B);

wherein said bromoisocyanurate is tribromoisocyanuric acid, dibromoisocyanuric acid, bromodichloroisocyanuric acid, dibromochloroisocyanuric acid, bromochloroisocyanuric acid, or any combination thereof;

wherein $Q^1$, $Q^2$, $Q^3$, $Q^4$, and $Q^5$, are each independently selected from: H, F, Cl, Br, COOH, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^2$, $N(R^1)SO_2R^1$, $N(acyl)_2$, $N[C(O)R^1]SO_2R^1$, $N[C(O)R^1]_2$, $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;

wherein each $R^1$ is independently aryl, alkyl, cycloalkyl or heterocyclyl; wherein $R^1$ is optionally substituted by one or more substituents of $R^2$;

wherein each $R^2$ is independently F, Cl, Br, COOH, acyl, aryl, alkyl, cycloalkyl or heterocyclyl;

wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Br.

In one embodiment, A of the organic bromide (1A) and of the carboxylic acid (2A) in scheme 1 is arene. In another embodiment, A of the organic bromide (1A) and the carboxylic acid (2A) in scheme 1 is an alkane. In another embodiment, A of the organic bromide (1A) and of the carboxylic acid (2A) in scheme 1 is a cycloalkane. In another embodiment, A of the organic bromide (1A) and of the carboxylic acid (2A) in scheme 1 is a saturated heterocycle.

In one embodiment the A is substituted with one or more substituents Q (in Scheme 1); where each Q is independently F, Cl, Br, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;

wherein each $R^1$ is independently aryl, alkyl, cycloalkyl or heterocyclyl, wherein $R^1$ is optionally substituted by one or more substituents of $R^2$;

wherein each $R^2$ is independently F, Cl, Br, COOH, acyl, aryl, alkyl, cycloalkyl or heterocyclyl.

In another embodiment, Q does not comprise electron donating substituents in the aromatic ring. Examples for electron donating substitutions include but not limited to: OH, $NH_2$, NH-alkyl, $N(alkyl)_2$.

In another embodiment, Q is at least one of $NO_2$, Cl, F, Br, CN, C(O)OMe, or $CF_3$.

In another embodiment, each Q is independently Cl. In another embodiment, each Q is independently F. In another embodiment, each Q is independently Br. In another embodiment, each Q is independently CN. In another embodiment, each Q is independently $CF_3$. In another embodiment, each Q is independently $CCl_3$. In another embodiment, each Q is independently acyl group. In another embodiment, each Q is independently $SO_3R^1$. In another embodiment, each Q is independently $SO_2R^1$. In another embodiment, each Q is independently $COR^1$. In another embodiment, each Q is independently $C(O)OR^1$. In another embodiment, each Q is independently C(O)OMe. In another embodiment, each Q is independently COCl. In another embodiment, each Q is independently amide. In another embodiment, each Q is independently $C(O)N(R^1)_2$. In another embodiment, each Q is independently $OCF_3$. In another embodiment, each Q is independently $R^1$. In another embodiment, each Q is independently alkyl. In another embodiment, each Q is independently t-Bu. In another embodiment, each Q is independently cycloalkyl. In another embodiment, each Q is independently heterocyclyl. In another embodiment, each Q is independently $OR^1$. In another embodiment, each Q is independently OMe. In another embodiment, each Q is independently $SR^1$. In another embodiment, each Q is independently SMe. In another embodiment, each Q is independently acetyl. In another embodiment, each Q is independently benzoyl. In another embodiment, each Q is independently mesyl. In another embodiment, each Q is independently tosyl. In another embodiment, each Q is independently $NO_2$. In another embodiment, each Q is independently $N(R^1)_3^+$. In another embodiment, each Q is independently O-acyl. In another embodiment, each Q is independently $OC(O)R^1$. In another embodiment, each Q is independently acetoxy. In another embodiment, each Q is independently $OSO_2R^1$. In another embodiment, each Q is independently mesyloxy. In another embodiment, each Q is independently tosyloxy. In another embodiment, each Q is independently S-acyl. In another embodiment, each Q is independently $SC(O)R^1$. In another embodiment, each Q is independently $N(R^1)$acyl. In another embodiment, each Q is independently $N(R^1)C(O)R^1$. In another embodiment, each Q is independently $N(R^1)SO_2R^1$. In another embodiment, each Q is independently $N(acyl)_2$. In another embodiment, each Q is independently $N[C(O)R^1]SO_2R^1$. In another embodiment, each Q is independently saccharinyl. In another embodiment, each Q is independently $N[C(O)R^1]_2$. In another embodiment, each Q is independently phthalimido. In another embodiment, each Q is independently aryl. In another embodiment, each Q is independently $C_6H_5$. In another embodiment, each Q is independently $C_6F_5$. In another embodiment, two vicinal Q substituents are joined to form a 5- or 6-membered substituted or unsubstituted, saturated or unsaturated heterocyclic ring. In another embodiment, two vicinal Q substituents are joined to form dihydrofuran-2,5-dione. In another embodiment, two vicinal Q substituents are joined to form pyrrolidine-2,5-dione. In another embodiment, if m>1 then Q substituents are the same. In another embodiment, if m>1 then Q substituents are different.

In one embodiment, A of the organic bromide (1A) and of the carboxylic acid (2A) in scheme 1 is a benzene. In another embodiment, A is cycloalkane. In another embodiment, A is a saturated heterocycle.

In another embodiment A of the organic bromide (1A) and of the carboxylic acid (2A) in scheme 1 is an alkane. In another embodiment, the alkane chain is linear. In another embodiment, the alkane chain is branched.

In one embodiment, the carboxylic acid (2A) in scheme 1 is not ECH(Z)—COOH, wherein E is acyl, $CO_2Z'$, $SO_2Z'$, $S(Z')_2^+$, or $N(Z')_3+$ and Z and Z' are each independently a hydrogen, alkyl or an aryl. In another embodiment, the carboxylic acid (2A) in scheme 1 is not ZCH=CH—COOH or ZC≡C—COOH, where Z is either a hydrogen, alkyl or an aryl, the latter two are optionally substituted. In another embodiment, the A in scheme 1 is not unsaturated heterocycle. In another embodiment, the A in scheme 1 is not alkene or alkyne. In another embodiment, the A in scheme 1 is not cycloalkene or cycloalkyne. In another embodiment, the Q in scheme 1 is not OH, $NH_2$, NHR, or $NR_2$ group.

In another embodiment, at least one of $Q^1$, $Q^2$, $Q^3$, $Q^4$, and/or $Q^5$ is F, Cl, Br, $CF_3$, $CCl_3$, CN, COOH, C(O)OMe, $NO_2$, phthalimide, $OCF_3$, and/or any two of $Q^1$ and $Q^2$, $Q^2$ and $Q^3$, $Q^3$ and $Q^4$, or $Q^4$ and $Q^5$, are joined to form a dihydrofuran-2,5-dione or pyrrolidine-2,5-dione ring.

In another embodiment, at least one of $Q^1$, $Q^2$, $Q^3$, $Q^4$, and $Q^5$ is $NO_2$. In another embodiment, at least one of $Q^1$, $Q^2$, $Q^3$, $Q^4$, and $Q^5$ is $CF_3$. In another embodiment, at least one of $Q^1$, $Q^2$, $Q^3$, $Q^4$, and $Q^5$ is CN. In another embodiment, at least one of $Q^1$, $Q^2$, $Q^3$, $Q^4$, and $Q^5$ is Cl. In another embodiment, at least one of $Q^1$, $Q^2$, $Q^3$, $Q^4$, and $Q^5$ is F. In another embodiment, at least one of $Q^1$, $Q^2$, $Q^3$, $Q^4$, and $Q^5$ is Br. In another embodiment, at least one of $Q^1$, $Q^2$, $Q^3$, $Q^4$, and $Q^5$ is phthalimide. In another embodiment, at least one of $Q^1$, $Q^2$, $Q^3$, $Q^4$, and $Q^5$ is C(O)OMe.

In one embodiment, $Q^1$ of formula (1B) and (2B) in scheme 2 is F. In another embodiment, $Q^1$ is H. In another embodiment, $Q^1$ is $CF_3$. In another embodiment, $Q^1$ is Cl. In another embodiment, $Q^1$ is Br. In another embodiment, $Q^1$ is $NO_2$. In another embodiment, $Q^1$ is $CO_2Me$. In another embodiment, $Q^1$ is phthalimide.

In one embodiment, $Q^2$ of formula (1B) and (2B) in scheme 2 is H. In another embodiment, $Q^2$ is F. In another embodiment, $Q^2$ is $CF_3$. In another embodiment, $Q^2$ is Cl. In another embodiment, $Q^2$ is Br. In another embodiment, $Q^2$ is CN. In another embodiment, $Q^2$ is $NO_2$. In another embodiment, $Q^2$ is $CO_2Me$. In another embodiment, $Q^2$ is COOH.

In one embodiment, $Q^3$ of formula (1B) and (2B) in scheme 2 is H. In another embodiment, $Q^3$ is CN. In another embodiment, $Q^3$ is Cl. In another embodiment, $Q^3$ is Br. In another embodiment, $Q^3$ is F. In another embodiment, $Q^3$ is $CF_3$. In another embodiment, $Q^3$ is $NO_2$. In another embodiment, $Q^3$ is $CO_2Me$. In another embodiment, $Q^3$ is COOH.

In one embodiment, $Q^4$ of formula (1B) and (2B) in scheme 2 is H. In another embodiment, $Q^4$ is F. In another embodiment, $Q^4$ is $CF_3$. In another embodiment, $Q^4$ is CN. In another embodiment, $Q^4$ is Cl. In another embodiment, $Q^4$ is $NO_2$.

In one embodiment, $Q^5$ of formula (1B) and (2B) in scheme 2 is H. In another embodiment, $Q^5$ is F. In another embodiment, $Q^5$ is $CF_3$. In another embodiment, $Q^5$ is CN. In another embodiment, $Q^5$ is Cl.

In one embodiment, $Q^3$ and $Q^4$ of formula (1B) and (2B) in scheme 2 are joined to form a 5- or 6-membered substituted or unsubstituted, saturated or unsaturated heterocyclic ring. In another embodiment, the heterocyclic ring is dihydrofuran-2,5-dione. In another embodiment, the heterocyclic ring is pyrrolidine-2,5-dione. In another embodiment, the heterocyclic ring is substituted with an alkyl. In another embodiment, the alkyl is t-Bu.

In one embodiment, m of scheme 1 and of compounds (1A) and (2A) is an integer number greater than or equal to 0. In another embodiment, m is 0. In another embodiment, m is 1. In another embodiment, m is 2. In another embodiment, m is 3. In another embodiment, if m>1 than Q can be different or the same.

In one embodiment, n of compounds (1A), (2A) in scheme 1 is an integer number greater than or equal to 1. In another embodiment, n is between 1 and 5. In another embodiment, n is between 1 and 3. In another embodiment, n is 1 or 2. In another embodiment, n is 1. In another embodiment, n is 2. In another embodiment, n is 3.

In one embodiment, this invention is directed to a process for the preparation of organic bromide from its corresponding carboxylic acid, said process comprises a radical bromodecarboxylation reaction of the carboxylic acid with a bromoisocyanurate, wherein said carboxylic acid is selected from the carboxylic acids listed in Tables 4, 5, 6 and 11 below.

According to this invention, the term "bromoisocyanurate" refers to tribromoisocyanuric acid, dibromoisocyanuric acid, bromodichloroisocyanuric acid, dibromochloroisocyanuric acid, bromochloroisocyanuric acid, or any combination thereof. In one embodiment, the bromoisocyanurate reagent used in the process of the invention is freshly prepared according to known procedures [Journal of the Swimming Pool and Spa Industry 2004, v. 5, 16]. In another embodiment, tribromoisocyanuric acid, dibromoisocyanuric acid, bromodichloroisocyanuric acid, dibromochloroisocyanuric acid, and/or bromochloroisocyanuric acid are stable. In another embodiment, dibromoisocyanuric acid is commercially available.

In one embodiment, the process of this invention, represented by schemes 1 and 2, has a radical mechanism. In another embodiment all factors that promote radical reaction may stimulate the process of this invention. Factors that promote radical reaction: heating, electromagnetic irradiation, addition of radical initiators In one embodiment, the reaction mixture of the process of this invention and the composition of this invention further comprises an additive. In another embodiment, the additive is bromine, a salt comprising bromide or a polybromide anion and an organic or inorganic cation; or any combination thereof. In another embodiment, the cation is a substituted or unsubstituted onium ion. The term "onium" refers in one embodiment to cations (with their counter-ions) derived by addition of a hydron to a mononuclear parent hydride of the nitrogen, chalcogen and halogen families. Non limiting examples of oniums include $[NH_4]^+$ ammonium, $[OH_3]^+$ oxonium, $[PH_4]^+$ phosphonium, $[SH_3]^+$ sulfonium, $[AsH_4]^+$ arsonium, $[SeH_3]^+$ selenonium, $[BrH_2]^+$ bromonium, $[SbH_4]^+)$ stibonium, $[TeH_3]^+)$ telluronium, $[IH_2]^+$ iodonium, $[BiH_4]^+$ bismuthonium.

Substituted oniums refers to substitution of the above parent ions by univalent groups or by two or three free valencies. E.g. $[SMe_3]^+$ trimethylsulfonium (a tertiary sulfonium ion), $[MePPh_3]^+$ methyltriphethylphosphonium (a quaternary phosphonium ion), $[HNEt_3]^+$ triethylammonium (a tertiary ammonium ion), $[NPr_4]^+$ tetrapropylammonium (a quaternary ammonium ion), $[R_2C=NR_2]^+$ iminium ions.

In one embodiment, the term "inorganic cation" used herein refers to alkali or alkaline earth metal cations, transition metal cation, or unsubstituted onium cation. In another embodiment, the inorganic cation is $Li^+$. In another embodiment, the inorganic cation is $Na^+$. In another embodiment, the inorganic cation is $K^+$. In another embodiment, the inorganic cation is $Rb^+$. In another embodiment, the inorganic cation is $Cs^+$. In another embodiment, the inorganic cation is $Zn^{2+}$. In another embodiment, the inorganic cation is $Cu^{2+}$. In another embodiment, the inorganic cation is ammonium cation $[Na_4]^+$.

In one embodiment, the term "organic cation" used herein refers to substituted onium cation. In another embodiment, the substituted onium cation is substituted ammonium cation, substituted phosphonium cation, substituted oxonium cation, substituted sulfonium cation, substituted arsonium cation, substituted selenonium cation, substituted telluronium cation, substituted iodonium cation, any other known onium cation, or any combination thereof. In another embodiment, the substituted ammonium cation is the substituted or unsubstituted guanidinium cation, substituted or unsubstituted pyridinium cation, substituted or unsubstituted amidinium cation, substituted or unsubstituted quaternary ammonium cation $[NR^1_4]^+$, substituted or unsubstituted tertiary ammonium cation $[HNR^1_3]^+$. In another embodiment, the substituted phosphonium cation is substituted or unsubstituted quaternary phosphonium cation $[PR^1_4]^+$, wherein $R^1$ is alkyl, aryl, cycloalkyl, heterocyclyl, or any combination thereof. In another embodiment, the quaternary ammonium cation $[NR^1_4]^+$ is tetraalkylammonium, trialkylarylammonium, dialkyldiarylammonium, trialkylbenzylammonium, or any combination thereof. In another embodiment, non-limiting examples of the quaternary ammonium cation $[NR^1_4]^+$ include tetrametylammonium, tetraethylammonium, tetrabutylammonium, tetraoctylammonium, trimethyloctylammonium, cetyltrimethylammonium, or any combination thereof. In another embodiment, the quaternary phosphonium cation $[PR^1_4]^+$ is tetraalkylphosphonium, alkyltriarylphosphonium, benzyltriarylphosphonium, benzyltrialkylphosphonium, or any combination thereof. In another embodiment, non-limiting examples of the quaternary phosphonium cation $[PR^1_4]^+$ include tetraphenylphosphonium, benzyltriphenylphosphonium, tetrabutylphosphonium, methyltriphenylphosphonium, benzyltributylphosphonium cation or any combination thereof. In another embodiment, the substituted sulfonium cation is substituted or unsubstituted tertiary sulfonium cation, substituted or unsubstituted sulfoxonium, thiopyrylium or thiuronium ion; or any combination thereof. In another embodiment the substituted oxonium cation is substituted or unsubstituted tertiary oxonium cation, substituted or unsubstituted pyrylium cation; or any combination thereof.

In another embodiment, substituted cations as referred herein are substituted with halide, nitrile, nitro, alkyl, aryl, cycloalkyl, heterocyclyl, amide, carboxylic acid, acyl or any combination thereof.

In one embodiment, the term "polybromide anion" used herein refers to a molecule or ion containing three or more bromine atoms or to an ion of formula $[Br_p]^{q-}$, where p is an integer of at least 3 and q is an integer of at least 1 and not more than p/2. In another embodiment, p is an integer between 3-24 and q is 1 or 2. In another embodiment p is 3, 5, 7, 9, 11 or 13 and q is 1. In another embodiment p is 4, 8, 20 or 24 and q is 2.

In another embodiment, the additive is $Br_2$, $[NPr_4]Br$, $[NPr_4]Br_3$, $[NPr_4]Br_9$, or any combination thereof.

An "alkyl" refers, in one embodiment, to a univalent groups derived from alkanes by removal of a hydrogen atom from any carbon atom: $C_nH_{2n+1}$—. In one embodiment, the alkyl group has 1-20 carbons. Examples for alkyls include but are not limited to: methyl, ethyl, propyl, isopropyl, butyl, isobutyl, s-butyl, tert-butyl, pentyl, neopentyl, octyl, isooctyl and the like The term "alkane" refers to acyclic branched or unbranched hydrocarbons having the general formula $C_nH_{2n+2}$, and therefore consisting entirely of hydrogen atoms and saturated carbon atoms. Examples of alkane include: methane, ethane, propane, n-butane, isobutane, n-pentane, neopentane, n-octane, isooctane and the like.

An "arene" refers to monocyclic and polycyclic aromatic hydrocarbons. Nonlimiting examples of arenes are benzene, biphenyl, naphthalene, anthracene, and the like.

An "aryl" group refers, to univalent groups derived from arenes by removal of a hydrogen atom from a ring carbon atom. Nonlimiting examples of aryl groups are phenyl, naphthyl, antracenyl, phenanthryl, and the like.

A "cycloalkyl" refers to univalent groups derived from cycloalkanes by removal of a hydrogen atom from a ring carbon atom Non limiting examples of cycloalkyl include: cyclobutyl, norbornyl, cyclopentyl and cyclohexyl.

A "cycloalkane" refers to saturated mono- or polycyclic hydrocarbons. A general chemical formula for cycloalkanes would be $C_nH_{2(n+1-g)}$ where n=number of C atoms and g=number of rings in the molecule.

A "heterocyclyl" refers to univalent groups formed by removing a hydrogen atom from any ring atom of a mono or polycyclic heterocyclic compound.

A "heterocycle" refers to a mono- or poly-cyclic heterocyclic compound consisting of carbon, hydrogen and at least one of nitrogen, sulfur, oxygen, phosphorous or combination thereof in one of the rings. In one embodiment, the heterocyclic compound consists 2-7 fused rings. Non limiting examples of monocyclic saturated heterocyclic compounds are aziridine, oxirane, thiirane, azetidine, oxetane, thietane, pyrrolidine, tetrahydrofurane, thiolane, pyperidine, oxane, thiane, azepane, oxepane, thiepane, imidazolidine, oxazolidine, thiazolidine, dioxolane, piperazine, morpholine, dioxane, homopiperazine. Non limiting examples of saturated bicyclic heterocyclic compounds are quinuclidine, 7-oxanorbornane, 7-thiabicyclo[2.2.1]heptane, 3-oxabicyclo[3.1.1] heptane, 3-azabicyclo[3.1.1]heptane, octahydroindole, octahydro-2-benzofuran.

An "amide" refers, in one embodiment, to a derivative of oxoacid in which an acidic hydroxyl group has been replaced by an amino or substituted amino group. Compounds having one or two acyl groups on a given nitrogen are generically included and may be designated as primary and secondary amides, respectively.

An "acyl" group is formed by removing one or more hydroxyl groups from oxoacids, and replacement analogues of such acyl groups. E.g. —C(=O)R, —C(=O)OR, —C(=O)NR$_2$, —C≡N, —S(=O)$_2$R, —S(=O)$_2$OR, —NO$_2$. Non limiting examples of the acyl groups include acetyl —C(O)Me, benzoyl —C(O)Ph, C(O)OMe, —C(=O) Cl, mesyl MeSO$_2$—, tosyl 4-MeC$_6$H$_4$SO$_2$—, A "carboxylic acid" refers, in one embodiment, to oxoacids having the structure RC(=O)OH.

In another embodiment, the bromodecarboxylation reaction represented by schemes 1 and 2 is conducted at room temperature. In another embodiment, the reaction is conducted under cooling. In another embodiment, the bromodecarboxylation reaction is initiated thermally. In another embodiment, the bromodecarboxylation reaction is further subjected to heat. In another embodiment, the bromodecarboxylation reaction is conducted at a temperature of between −20° C. and 150° C. In another embodiment, said process is conducted at a temperature of between about 0° C. and about 100° C.

In another embodiment, the process of this invention further comprising the use of radical initiator in the reaction. In another embodiment, the radical initiator is an azo compound or organic peroxide. In another embodiment, the azo compound is azobisisobutyronitrile (AIBN) or 1,1'-azobis (cyclohexanecarbonitrile) (ABCN). In another embodiment, the organic peroxide is benzoyl peroxide.

In another embodiment, the bromoarene of formula (1A) and/or (1B) is prepared according to process described in Examples 3-11.

In one embodiment, the process of this invention, represented by schemes 1 and 2, is conducted under electromagnetic irradiation. In another embodiment, the electromagnetic radiation is visible light, infrared radiation, ultraviolet radiation, microwave radiation or any combination thereof.

In another embodiment, the source of the visible light is sunlight, fluorescent lamp, light-emitting diode, incandescent lamp or any combination thereof.

The term "irradiation" refers in one embodiment to the energy that is irradiated or transmitted in the form of rays or waves or particles. Electromagnetic irradiation refers to radiation consisting of waves of energy associated with electric and magnetic fields resulting from the acceleration of an electric charge. Ultrasound refers to cyclic mechanical vibrations with a frequency greater than 20 kilohertz (20,000 hertz). Ultraviolet irradiation refers to electromagnetic radiation with wavelengths 100 to 400 nm. Visible irradiation (light, visible light) refers to electromagnetic irradiation with wavelengths 400 to 780 nm. Infrared irradiation refers to electromagnetic irradiation with wavelengths 780 to 20000 nm. Microwave irradiation refers to electromagnetic irradiation with wavelengths 2 to 1000 mm.

Devices serving as a source of the electromagnetic irradiation include a mercury lamp, a xenon lamp, a carbon arc lamp, an incandescent lamp, a tungsten lamp, a fluorescent lamp, light-emitting diode, and sunlight, and the like.

Tungsten lamp refers to incandescent lamp that generates light by passing an electric current through a thin filament wire (usually of wolfram) until it is extremely hot. The lamps are often filled by a halogen gas such as iodine and bromine that allow filaments to work at higher temperatures and higher efficiencies.

Light-emitting diode (LED) refers to a semiconductor (often a combination of gallium, arsenic, and phosphorous or gallium and nitrogen) containing an n region (where electrons are more numerous than positive charges) separated from a p region (where positive charges are more numerous than negative charges). Upon application of a voltage, charges move and emission of ultraviolet, visible, or infrared radiation is produced each time a charge recombination takes place. Although an LED emits incoherent monochromatic light, normally a very narrow frequency range is obtained.

In another embodiment, the process is conducted in the presence of an organic or an inorganic solvent or combination thereof and the composition of this invention comprises an organic or an inorganic solvent or combination thereof. In another embodiment, the organic solvent is $CH_3CN$, $CH_3NO_2$, ester, a hydrocarbon solvent, or halocarbon solvent or combination thereof. In another embodiment the halocarbon solvent is $CH_2Cl_2$, $Cl(CH_2)_2Cl$, $CHCl_3$, $CCl_4$, $C_6H_5Cl$, o-$C_6H_4Cl_2$, $BrCCl_3$, $CH_2Br_2$, $CFCl_3$, $CF_3CCl_3$, $ClCF_2CFCl_2$, $BrCF_2CFClBr$, $CF_3CClBr_2$, $CF_3CHBrCl$, $C_6H_5F$, $C_6H_5CF_3$, 4-$ClC_6H_4CF_3$, 2,4-$Cl_2C_6H_3CF_3$ or any combination thereof. In another embodiment, the solvent is $CH_2Cl_2$ or $BrCCl_3$. In another embodiment, the solvent is a polar solvent. In another embodiment, the solvent is a nonpolar solvent. In another embodiment, the solvent is a hydrocarbon. In another embodiment, the solvent is benzene $C_6H_6$ (PhH). In another embodiment, the solvent is acetonitrile $CH_3CN$ (MeCN). In another embodiment, the solvent is ethyl acetate EtOAc. In another embodiment, the solvent is halocarbon. In another embodiment, the solvent is carbon tetrachloride $CCl_4$. In another embodiment, the solvent is chloroform $CHCl_3$. In another embodiment, the solvent is bromotrichloromethane $BrCCl_3$. In another embodiment, the solvent is dibromomethane $CH_2Br_2$. In another embodiment, the solvent is trichlorofluoromethane $CFCl_3$. In another embodiment, the solvent is 1,1,1-trichlorotrifluoroethane $CF_3CCl_3$. In another embodiment, the solvent is 1,1,2-trichlorotrifluoroethane $ClCF_2CFCl_2$. In another embodiment, the solvent is 1,2-dibromo-1-chlorotrifluoroethane $BrCF_2CFClBr$. In another embodiment, the solvent is 1,1-dibromo-1-chlorotrifluoroethane $CF_3CClBr_2$. In another embodiment, the solvent is 2-bromo-2-chloro-1,1,1-trifluoroethane $CF_3CHBrCl$ (halothane). In another embodiment, the solvent is fluorobenzene $C_6H_5F$ (PhF). In another embodiment, the solvent is chlorobenzene $C_6H_5Cl$ (PhCl). In another embodiment, the solvent is benzotrifluoride $C_6H_5CF_3$ ($PhCF_3$). In another embodiment, the solvent is p-chlorobenzotrifluoride 4-$ClC_6H_4CF_3$. In another embodiment, the solvent is 1,2-dichloroethane $Cl(CH_2)_2Cl$ (DCE). In another embodiment, the solvent is ortho-dichlorobenzene o-$C_6H_4Cl_2$. In another embodiment, the solvent is dichloromethane $CH_2Cl_2$ (DCM). In another embodiment, the solvent is 2,4-dichlorobenzotrifluoride 2,4-$Cl_2C_6H_3CF_3$. In another embodiment, bromodecarboxylation process is preferably conducted in a halocarbon solvent. In another embodiment, bromodecarboxylation process is preferably conducted in a $BrCCl_3$, $CH_2Cl_2$, $CH_2Br_2$, $CF_3CHBrCl$ or any combination thereof.

The term "hydrocarbon solvent" refers to any solvent consisting of the carbon and hydrogen elements. Non limiting examples of hydrocarbon solvents are cyclohexane, heptane, pentane, hexane, or benzene $C_6H_6$.

The term "halocarbon solvent" refers to any solvent wherein one or more of the carbons are covalently linked to one or more halogens (fluorine, chlorine, or bromine). Non limiting examples of halocarbon solvents are chloroform $CHCl_3$, dichloromethane $CH_2Cl_2$ (DCM), bromotrichloromethane $BrCCl_3$, chlorobenzene $C_6H_5Cl$ (PhCl), ortho-dichlorobenzene o-$C_6H_4Cl_2$, 1,2-dichloroethane $Cl(CH_2)_2Cl$ (DCE), carbon tetrachloride $CCl_4$, 1,3-dichloropropane $Cl(CH_2)_3Cl$, 1,1,2,2-tertrachlorodifluoroethane $FCCl_2CCl_2F$, 1,1,2-trichloroethane $CHCl_2CH_2Cl$, bromobenzene $C_6H_5Br$, 1,1,2-trichlorotrifluoroethane $ClCF_2CFCl_2$, dibromomethane $CH_2Br_2$, 2-bromo-2-chloro-1,1,1-trifluoroethane $CF_3CHBrCl$ (halothane), 1,2-dibromoethane $Br(CH_2)_2Br$, benzotrifluoride $C_6H_5CF_3$ ($PhCF_3$), 2,4-dichlorobenzotrifluoride 2,4-$Cl_2C_6H_3CF_3$.

In one embodiment, following the formation of organic bromide, or the compound of formula (1A) or (1B) the organic bromide is isolated from the reaction mixture by filtration, washing, chromatography, crystallization or any combination thereof. In another embodiment the bromo compound is isolated from the reaction mixture by filtration followed by a washing step. In another embodiment the washing step comprises washing with an aqueous reducing agent followed by washing with an aqueous base. In another embodiment the washing step comprises washing with an aqueous base followed by washing with an aqueous reducing agent. In another embodiment, the washing step comprises washing with an aqueous reducing agent and a base.

In one embodiment the organic bromide is isolated from the reaction mixture by a washing step.

In another embodiment, the washing step comprises treating of the reaction mixture with reducing agent, wherein excess of the bromoisocyanurate is converted to cyanuric acid insoluble in non-polar organic solvents, and thereby can be removed from the organic phase. In another embodiment, an aqueous reducing agent refers to an aqueous solution comprising a reducing agent. Non limiting examples of reducing agents are $Na_2SO_3$, $NaHSO_3$, $Na_2S_2O_3$, $NaBH_4$/NaOH or combination thereof. In another embodiment the reducing agent is added at a concentration of between 1-10% w/w to the water to obtain an aqueous reducing agent solution.

In one embodiment, the process of this invention directed to bromodecarboxylation comprising a washing step with an aqueous reducing agent. In another embodiment, following the washing step a potassium iodide starch paper test is performed to identify traces of the bromoisocyanurate. "A potassium iodide starch paper test" (SPT) refers to a starch iodide test paper that has been wetted with aqueous acetic acid; 1:1; v/v]. In another embodiment, if the test is positive, an additional aqueous reducing agent is added to the reaction mixture.

In another embodiment the washing step comprises washing the product with a mild aqueous base wherein the unreacted carboxylic acid is removed from the organic phase by washing with an aqueous base. In another embodiment, the carboxylic acid is recovered by acidifying the aqueous phase. In another embodiment, an aqueous base refers to an aqueous solution comprising a base. Non limiting examples of a base is $NaHCO_3$, $NaOH$, $Na_2CO_3$, $KOH$, $Na_2SO_3$ or combination thereof. In another embodiment the base is added at a concentration of between 1-10% w/w to the water to obtain an aqueous base solution.

In another embodiment, the washing step with an aqueous reducing agent is conducted before the washing step with the aqueous base. In another embodiment, the washing step with the aqueous base is conducted before the washing step with the aqueous reducing agent. In another embodiment, the washing step comprises washing with an aqueous reducing agent and a base.

Such a combination of an aqueous reducing agent and a base includes $Na_2SO_3$ and $NaBH_4/NaOH$ which are basic reducing agents that combine properties of reducing agent and a base.

In another embodiment, the washing steps of this invention are conducted using the organic solvent of the reaction mixture as the organic phase. In another embodiment, the washing step with the aqueous base and the washing step with the aqueous reducing agent are independently performed using a) the organic solvent of the reaction mixture, b) a mixture of organic solvents, or c) a different organic solvent, as the organic phase. Non limiting examples of organic solvents used as an organic phase in the washing step are hydrocarbon solvent, halocarbon solvent, or esters such as cyclohexane, heptane, hexane, pentane, benzene, toluene, chlorobenzene, 1,2-dichloroethane, carbon tetrachloride, 1,3-dichloropropane, 1,1,2,2-tertrachlorodifluoroethane, 1,1,2-trichloroethane, trichloroethylene, perchloroethylene, dichloromethane, chloroform, ethyl acetate or butyl acetate.

In one embodiment, following the washing step, the aqueous phase is treated with an acid or an aqueous acid solution to precipitate solid cyanuric acid.

In one embodiment, the organic bromide product of the bromodecarboxylation reaction is soluble in organic phase and not soluble in the aqueous phase. In another embodiment, the crude organic bromide is isolated from reaction mixture by standard organic solvent extractive work-up.

In one embodiment, removing the solvent from the organic phase gives the crude desired bromide product as the residue. In another embodiment, the residue is the pure desired bromide product. In another embodiment, the bromide is purified by crystallization, rectification or chromatography of the residue.

In another embodiment the isolation and purification further comprises a drying step. In another embodiment the purification further comprises chromatography.

In one embodiment, the process of this invention provides a process for the preparation of pure organic bromide.

In another embodiment, the "pure bromide" refers to 92% or more purity. In another embodiment, the "pure bromide" refers to about 95% or more purity. In another embodiment, the "pure bromide" refers to about 90% or more purity. In another embodiment, the "pure bromide" refers to about 85% or more purity. In another embodiment, the "pure bromide" refers to about 99% or more purity. In another embodiment, the "pure bromide" refers to about 98% or more purity. In another embodiment, the "pure bromide" refers to about 97% or more purity.

In one embodiment, this invention is directed to organic bromide compound represented by the formula (1A) or (1B) having purity of about 99% or more, prepared according to the process of this invention. In another embodiment, this invention is directed to organic bromide compound represented by the formula (1A) or (1B) having purity of about 98% or more prepared according to the process of this invention. In another embodiment, this invention is directed to organic bromide compound represented by the formula (1A) or (1B) having purity of about 90% or more, prepared according to the process of this invention. In another embodiment, this invention is directed to organic bromide compound represented by the formula (1A) or (1B) having purity of about 95% or more, prepared according to the process of this invention. In another embodiment, this invention is directed to organic bromide compound represented by the formula (1A) or (1B) having purity of about 85% or more, prepared according to the process of this invention. In another embodiment, this invention is directed to organic bromide compound represented by the formula (1A) or (1B) having purity of about 97% or more, prepared according to the process of this invention.

In one embodiment, the process of this invention, represented by schemes 1 and 2, provides a yield of 60% or more. In another embodiment, the process of this invention provides a yield of 70% or more. In another embodiment, the process of this invention provides a yield of 80% or more. In another embodiment, the process of this invention provides a yield of 85% or more. In another embodiment, the process of this invention provides a yield of 90% or more. In another embodiment, the process of this invention provides a yield of 95% or more.

In one embodiment, this invention is directed to a process comprising reacting carboxylic acid of formula (2A) or (2B) with bromoisocyanurate and an additive in a certain molar ratio. In another embodiment, the carboxylic acid compounds (2A) or (2B) can have more than one carboxylic acid groups.

In one embodiment the bromoisocyanurate: (each carboxylic group of the carboxylic acid of formula (2A)) molar ratio is between 0.1 and 2. In another embodiment the bromoisocyanurate: (each carboxylic group of the carboxylic acid of formula (2A)) molar ratio is between 1 and 2. In another embodiment the bromoisocyanurate: (each carboxylic group of the carboxylic acid of formula (2A)) molar ratio is between 0.1 and 1. In another embodiment the bromoisocyanurate: (each carboxylic group of the carboxylic acid of formula (2A)) molar ratio is 1. In another embodiment the bromoisocyanurate: (each carboxylic group of the carboxylic acid of formula (2A)) molar ratio is between 1 and 1.5.

In one embodiment, the reaction mixture of the process according to this invention, further comprises an additive. In another embodiment, the additive: (each carboxylic group of the carboxylic acid of formula (2A)) molar ration is between 0.1 and 4. In another embodiment, additive: (each carboxylic group of the carboxylic acid of formula (2A)) molar ration is between 1 and 4. In another embodiment, the additive: ((each carboxylic group of the carboxylic acid of formula (2A)) molar ration is between 0.1 and 2. In another embodiment, the additive: (each carboxylic group of the carboxylic acid of formula (2A)) molar ration is between 0.1 and 1. In another embodiment the additive: (each carboxylic group of the carboxylic acid of formula (2A)) molar ration is between 1 and 2. In another embodiment the additive: (each carboxylic group of the carboxylic acid of formula (2A)) molar ration is between 1 and 3.

In one embodiment, this invention is directed to a radiation-sensitive composition comprising carboxylic acid of formula (2A)

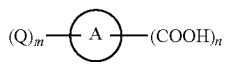

2A and bromoisocyanurate which generates organic bromide of formula (1A)

1A upon electromagnetic irradiation,
wherein
the bromoisocyanurate is tribromoisocyanuric acid, dibromoisocyanuric acid, bromodichloroisocyanuric acid, dibromochloroisocyanuric acid, bromochloroisocyanuric acid, or any combination thereof;
A is arene, alkane, cycloalkane or saturated heterocycle;
n is an integer of at least 1;
m is an integer of at least 0;
each Q is independently F, Cl, Br, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)acyl$, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;
wherein each $R^1$ is independently aryl, alkyl, cycloalkyl or heterocyclyl, wherein $R^1$ is optionally substituted by one or more substituents of $R^2$;
wherein each $R^2$ is independently F, Cl, Br, COOH, acyl, aryl, alkyl, cycloalkyl or heterocyclyl;
wherein if either one of $R^2$ in (2A) is a carboxylic group COOH, then the respective $R^2$ in (1A) is Br;
wherein said position of Br and Q in said structure of formula (1A) correspond to the same position of said COOH and Q, respectively in said structure of formula (2A)

In another embodiment A of formula (1A) or (2A) is arene. In another embodiment A of formula (1A) or (2A) is an alkane. In another embodiment A of formula (1A) or (2A) is cycloalkane or saturated heterocycle.

In another embodiment, this invention is directed to a radiation-sensitive composition comprising a carboxylic acid and bromoisocyanurate; wherein said carboxylic acid is represented by the structure of compound (2B):

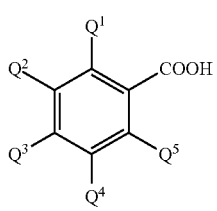

2B wherein $Q^1$, $Q^2$, $Q^3$, $Q^4$, and $Q^5$, are each independently selected from: H, F, Cl, Br, COOH, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)acyl$, $N(R^1)C(O)R^2$, $N(R^1)SO_2R^1$, $N(acyl)_2$, $N[C(O)R^1]SO_2R^1$, $N[C(O)R^1]_2$, $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;
wherein each $R^1$ is independently aryl, alkyl, cycloalkyl or heterocyclyl; wherein $R^1$ is optionally substituted by $R^2$;
wherein each $R^2$ is independently F, Cl, Br, COOH, acyl, aryl, alkyl, cycloalkyl or heterocyclyl;
wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Br.

In one embodiment, this invention is directed to a composition comprising an organic bromide of formula (1A):

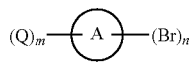

1A wherein said organic bromide of formula (1A) is prepared by reacting a carboxylic acid of formula (2A)

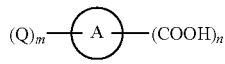

2A and bromoisocyanurate by electromagnetic irradiation;
wherein A is arene, alkane, cycloalkane or saturated heterocycle;
n is an integer of at least 1;
m is an integer of at least 0;
each Q is independently F, Cl, Br, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)acyl$, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;
wherein each $R^1$ is independently aryl, alkyl, cycloalkyl or heterocyclyl, wherein $R^1$ is optionally substituted by one or more substituents of $R^2$;
wherein each $R^2$ is independently F, Cl, Br, COOH, acyl, aryl, alkyl, cycloalkyl or heterocyclyl;
wherein if either one of $R^2$ in (2A) is a carboxylic group COOH, then the respective $R^2$ in (1A) is Br;
wherein said position of Br and Q in said structure of formula (1A) correspond to the same position of said COOH and Q, respectively in said structure of formula (2A)

In one embodiment, this invention is directed to a composition comprising an organic bromide of formula (1B):

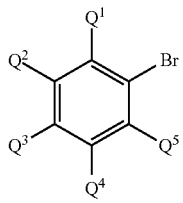

wherein said organic bromide of formula (1B) is prepared by reacting a carboxylic acid of formula (2B)

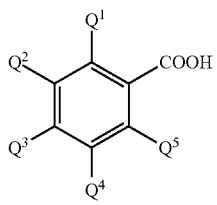

and bromoisocyanurate by electromagnetic irradiation;
wherein $Q^1$, $Q^2$, $Q^3$, $Q^4$, and $Q^5$, are each independently selected from: H, F, Cl, Br, COOH, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3{}^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^2$, $N(R^1)SO_2R^1$, $N(acyl)_2$, $N[C(O)R^1]SO_2R^1$, $N[C(O)R^1]_2$, $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;
wherein each $R^1$ is independently aryl, alkyl, cycloalkyl or heterocyclyl; wherein $R^1$ is optionally substituted by $R^2$;
wherein each $R^2$ is independently F, Cl, Br, COOH, acyl, aryl, alkyl, cycloalkyl or heterocyclyl;
wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Br.

Mechanism of the Bromodecarboxylation Reaction of the Invention

Without bounding to any particular mechanism or theory, it is contemplated that the process according to this invention is described as follows:

i. Bromination of the carboxylic acid $R$—$CO_2H$ (corresponds to compounds of formula (2A) and (2B)) with the bromoisocyanurate to give the corresponding acyl hypobromite, $R$—$CO_2Br$, according to equation (1):

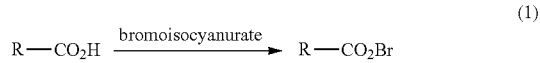

(1)

ii. Homolytic degradation of the acyl hypobromite, $R$—$CO_2Br$, to give carbon-centered free radical $R\cdot$ according to equation (2):

$R$—$CO_2Br \rightarrow R\cdot + CO_2 + Br\cdot$ (2)

iii. $R\cdot$ pulls out a bromine atom from nearest bromine atom donor to yield bromide $R$—$Br$ according to equation (3):

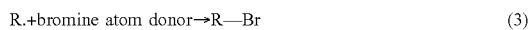

(3)

wherein the bromine atom donor is selected from: bromine radical $Br\cdot$ (equation (2)), additive (e.g. $Br_2$, bromide, polybromides), or the halocarbon solvent (e.g., $BrCCl_3$, $CF_3CHBrCl$).

It should be noted that the suggested mechanism presented above, is only a rough scheme of the complex real processes.

One indication for the radical chain mechanism of the bromodecarboxylation reaction is by using a 2,2,6,6-tetramethyl-1-piperidinynyloxyl (TEMPO) carbon-centered radical scavenger as a mechanistic diagnostic tool. Addition of TEMPO as radical chain inhibitor to the initial reaction mixture of the bromodecarboxylation reaction, inhibits the reaction. Inhibition of the bromodecarboxylation reaction by addition of TEMPO indicates that the reaction has a radical chain mechanism.

According to the present invention, the carbon-centered free radicals $R\cdot$ are obtained by applying photochemical and/or thermal energy to a mixture of carboxylic acid $R$—$CO_2H$, bromoisocyanurate and, optionally an additive. The photochemical energy increases the rate of the reaction.

The following examples are presented in order to more fully illustrate the preferred embodiments of the invention. They should in no way, however, be construed as limiting the broad scope of the invention.

EXAMPLES

Experimental Details

Reagents:

All reagents and solvents were purchased from Sigma-Aldrich, Alfa Aesar, Acros Organics, and TCI unless specified otherwise. 3,5,5-Trimethylhydantoin 3,5,5-TMH and 4,4-dimethyl-2-oxazolidinone DMO were prepared according to published procedure (WO2015068159 A2).

Techniques:

All reactions were performed under nitrogen atmosphere in non-flame dried glassware. Mounted nearby the reaction flask 3 W LED warm-white lamp was used for irradiation of the reaction mixture. Conversions were determined by $^1$H NMR, and yields of isolated product refer to products with more than 95% purity by $^1$H NMR. Flash column chromatography was performed employing 63-200 μm silica gel 60 according to standard techniques (*J. Org. Chem.* 1978, v. 43, 2923).

Analytical Methods:

GC analyses were performed on Shimadzu GC-2010 gas chromatograph with flame ionization detector (FID) using a 30 m×0.25 mm Quadrex capillary column with methyl 5% phenyl silicone stationary phase, 0.25 μm film thickness. For TLC analysis, Merck precoated TLC plates (silica gel 60 F-254 on glass plates, 0.25 mm) were used. NMR spectra were recorded on a Bruker AM-400 ($^1$H at 400 MHz, $^{13}$C at 100 MHz) instruments using $CDCl_3$ (unless otherwise stated) as a solvent. Data are reported as follows: chemical shift in ppm relative to internal TMS, multiplicity, coupling constant in Hz and integration. Compounds described in the literature were characterized by comparing their $^1$H and/or $^{13}$C NMR spectra to the previously reported data. New compounds were further characterized by high-resolution mass spectra.

The following abbreviations are used:
1,5,5-TMH=1,5,5-trimethylhydantoin
1-BTMH=1-bromo-3,5,5-trimethylhydantoin
3,5,5-TMH=3,5,5-trimethylhydantoin
3-BTMH=3-bromo-1,5,5-trimethylhydantoin ABCN=1,1'-azobis(cyclohexanecarbonitrile)
AIBN=azobisisobutyronitrile
Alk=alkyl
APCI=atmospheric pressure chemical ionization
Ar=arene
BDMO=3-bromo-4,4-dimethyl-2-oxazolidinone or 3-bromo-4,4-dimethyloxazolidin-2-one
BNPT=N-bromo-4-nitrophthalimide
BPT=N-bromophthalimide
BNPT=N-bromo-4-nitrophthalimide
CTAB=cetyltrimethylammonium bromide
d=doublet
DBDMH=1,3-dibromo-5,5-dimethylhydantoin
DBI=dibromoisocyanuric acid
DCE=1,2-dichloroethane
DCM=dichloromethane
DMO=4,4-dimethyl-2-oxazolidinone or 4,4-dimethyloxazolidin-2-one
FL=fluorescent room lighting
hv=visible light irradiation
HRMS=high resolution/accurate mass spectrometer
LED=light-emitting diode
LL=LED lamp irradiation
m=multiplet
MBCA=monobromoisocyanuric acid
MCCA=monochloroisocyanuric acid
N-bromoimide=bromoimide, wherein bromine atom is attached directly to nitrogen atom
NBS=N-bromosuccinimide
NBSac=N-bromosaccharine
NL=dark
NMR=nuclear magnetic resonance
ppm=part per million
rt=room temperature
s=singlet
SDS=sodium dodecyl sulfate
t=triplet
TL=tungsten lamp irradiation
TBCA=tribromoisocyanuric acid
TEMPO=2,2,6,6-tetramethyl-1-piperidinyloxy, free radical
Δ=heating Example 1

Preparation of N-bromoamides

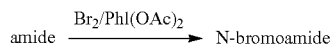

General Method A:

A mixture of amide (1.0 mmol), PhI(OAc)$_2$ (0.6 mmol), Br$_2$ (0.8 mmol), and MeCN (5-10 mL) was stirred at rt for 3-40 h and then concentrated in vacuo. CCl$_4$, cyclohexane, or benzene (5-10 mL) was added to the residue and the obtained mixture was stirred for 15 min at rt and 1 h at 0 to 5° C. The precipitated solid was filtered, washed on the filter with cold CCl$_4$, cyclohexane, or benzene and dried in vacuo to give the desired N-bromoimide as an off-white powder.

General Method B:

A mixture of amide (1.0 mmol), PhI(OAc)$_2$ (0.6 mmol), Br$_2$ (0.8 mmol), and CCl$_4$, benzene, or cyclohexane (5-10 mL) was stirred for 4-40 h at rt and for 1 h at 0 to 5° C. The precipitated solid was filtered, washed on the filter with cold CCl$_4$, benzene, or cyclohexane and dried in vacuo to give N-bromoimide as an off-white powder. The results are listed in Table 1.

Note:

In cases where more than one N—H group exists in the amide starting material, the amounts of PhI(OAc)$_2$ and Br$_2$ is multiplied by the number of N—H groups.

TABLE 1

Preparation of N-bromoamides

| entry | amide | Method | N-Bromo-amide | Yield, % |
|---|---|---|---|---|
| 1 | succinimide | A | NBS | 92 |
| 2 | succinimide | B | NBS | up to 94 |
| 3 | saccharin | A | NBSac | 86 |
| 4 | saccharin | B | NBSac | 50 |
| 5 | pthalimide | A | BPT | 90 |
| 6 | pthalimide | B | BPT | 70 |
| 7 | 4-nitrophthalimide | A | BNPT | 88 |
| 8 | 4-nitrophthalimide | B | BNPT | 90 |
| 9 | DMH | B | DBDMH | 97 |
| 10 | DPH | A | DBDPH | 80 |
| 11 | 3,5,5-TMH | A | 1-BTMH | 86 |
| 12 | DMO | A | BDMO | 84 |
| 13 | DMO | B | BDMO | up to 76 |

Entries 1-2: N-Bromosuccinimide, NBS $^1$H NMR: δ 2.96 (s, 4H) ppm; $^{13}$C NMR: δ 173.2, 28.8 ppm.

Entries 3-4: N-Bromosaccharin, NBSac $^1$H NMR (CD$_3$CN): δ 8.10-8.00 (m, 2H), 7.99-7.87 (m, 2H) ppm; $^{13}$C NMR (CD$_3$CN): δ 159.6, 139.3, 136.5, 135.9, 128.2, 126.4, 122.5 ppm.

Entries 5-6: N-Bromophthalimide, BPT $^1$H NMR (CD$_3$CN): δ 7.84-7.76 (m, 4H) ppm; $^{13}$C NMR (CD$_3$CN): δ 166.7, 135.3, 133.4, 124.2 ppm.

Entries 7-8: N-Bromo-4-nitrophthalimide, BNPT $^1$H NMR (CD$_3$CN): δ 8.58 (d, J=8.5 Hz, 1H), 8.55 (s, 1H) 8.04 (d, J=8.5 Hz, 1H) ppm; $^{13}$C NMR (CD$_3$CN): δ 165.2, 164.9, 152.6, 137.6, 134.3, 130.5, 125.6, 119.3 ppm.

Entry 9: 1,3-Dibromo-5,5-dimethylhydantoin in benzene, DBDMH $^1$H NMR: δ 1.46 (s, 6H) ppm; $^{13}$C NMR: δ 172.2, 151.5, 68.9, 23.9 ppm.

Entry 10: 1,3-Dibromo-5,5-diphenylhydantoin, DBDPH $^1$H NMR (CD$_3$CN): δ 7.51-7.43 (m, 6H), 7.32-7.28 (m, 4H) ppm; $^{13}$C NMR (CD$_3$CN): δ 171.4, 153.3, 137.0, 130.5, 129.7, 129.6, 129.3, 129.2, 80.1 ppm.

Entry 11: 1-Bromo-3,5,5-trimethylhydantoin, 1-BTMH $^1$H NMR: δ 3.06 (s, 3H), 1.38 (s, 6H) ppm; $^{13}$C NMR: δ 174.7, 155.1, 66.1, 26.0, 23.3 ppm.

Entries 12-13: 3-Bromo-4,4-dimethyl-2-oxazolidinone, BDMO $^1$H NMR: δ 4.19 (s, 2H), 1.29 (s, 6H) ppm; $^{13}$C NMR: δ 157.3, 74.8, 62.9, 24.1 ppm Example 2

Comparative Examples

A. Attempts to Bromodecarboxylate Arenecarboxylic Acids with N-Bromosuccinimide (NBS) Under Heterolytic Reaction Conditions Disclosed in IN803DEL1999

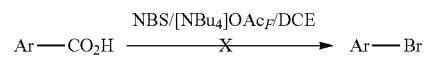

The reactions were conducted under fluorescent room lighting (FL).

Example 2A-1

An attempt to bromodecarboxylate benzoic acid using tetrabutylammonium trifluororacetate as catalyst

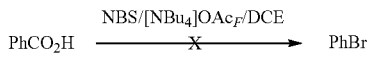

A mixture of benzoic acid (0.44 g, 3.60 mmol), N-bromosuccinimide NBS (0.60 g, 3.37 mmol), tetrabutylammonium trifluororacetate [NBu$_4$]OAc$_F$ (0.24 g, 0.67 mmol) and 1,2-dichloroethane DCE (6 mL) was stirred at rt for 24 h. The reaction mixture was washed with 1 M aq Na$_2$SO$_3$, dried over Na$_2$SO$_4$, and filtered through short neutral alumina pad.

The obtained filtrate did not contain bromobenzene (GC data, 1-chlro-2-fluorobenzene was used as internal standard).

Example 2A-2

An attempt to bromodecarboxylate p-toluic acid using tetrabutylammonium trifluororacetate as catalyst

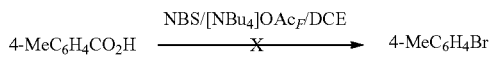

A mixture of p-toluic acid (0.48 g, 3.52 mmol), N-bromosuccinimide NBS (0.60 g, 3.37 mmol), tetrabutylammonium trifluororacetate [NBu$_4$]OAc$_F$ (0.24 g, 0.67 mmol) and 1,2-dichloroethane DCE (6 mL) was stirred at rt for 20 h. The reaction mixture was washed with 1 M aq Na$_2$SO$_3$, dried over Na$_2$SO$_4$, and filtered through short neutral alumina pad.

The obtained filtrate did not contain p-bromotoluene (GC data, o-dichlorobenzene was used as internal standard).

Example 2A-3

An attempt to bromodecarboxylate p-anisic acid using tetrabutylammonium trifluororacetate as catalyst

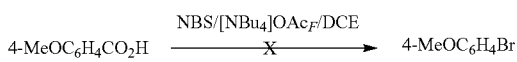

A mixture of p-anisic acid (0.52 g, 3.42 mmol), N-bromosuccinimide NBS (0.60 g, 3.37 mmol), tetrabutylammonium trifluororacetate [NBu$_4$]OAc$_F$ (0.24 g, 0.67 mmol) and 1,2-dichloroethane DCE (6 mL) was stirred at rt for 18 h. The reaction mixture was washed with 1 M aq Na$_2$SO$_3$, dried over Na$_2$SO$_4$, and filtered through short neutral alumina pad.

The obtained filtrate did not contain p-bromoanisol (GC data, 1,2,4-trichlorobenzene was used as internal standard).
B. Attempts to Bromodecarboxylate Arenecarboxylic Acids with N-Bromosuccinimide (NBS) Under Heterolytic Reaction Conditions Disclosed in *J. Dispersion Sci. Technol.* 2007, v. 28, 613

Example 2B-1

An attempt to bromodecarboxylate 2-bromobenzoic acid using cetyltrimethylammonium bromide as catalyst

A mixture of 2-bromobenzoic acid (0.20 g, 1.0 mmol), N-bromosuccinimide NBS (0.27 g, 1.5 mmol), cetyltrimethylammonium bromide CTAB (1.82 g, 5.0 mmol) and 1,2-dichloroethane DCE (10 mL) was stirred under reflux conditions in dark for 3 h. After it was cooled, the reaction mixture was washed with 1 M aq Na$_2$SO$_3$, dried over Na$_2$SO$_4$, filtered through short neutral alumina pad and concentrated in vacuo to give 0.21 g (79%) of 2-chloroethyl 2-bromobenzoate 2-BrC$_6$H$_4$CO$_2$(CH$_2$)$_2$Cl.

$^1$H NMR: δ 7.85 (d, J=7 Hz, 1H), 7.64 (d, J=7 Hz, 1H), 7.38-7.28 (m, 2H) 4.56 (t, J=6 Hz, 2H), 3.80 (t, J=6 Hz, 2H) ppm.

Example 2B-2

An attempt to bromodecarboxylate 2-bromobenzoic acid using sodium dodecyl sulfate as catalyst

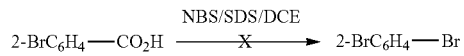

A mixture of 2-bromobenzoic acid (0.20 g, 1.0 mmol), N-bromosuccinimide NBS (0.27 g, 1.5 mmol), sodium dodecyl sulfate SDS (1.44 g, 5.0 mmol) and 1,2-dichloroethane DCE (10 mL) was stirred in dark for 3 h under reflux conditions. After it was cooled, the reaction mixture was washed with 1 M aq Na$_2$SO$_3$, dried over Na$_2$SO$_4$, filtered through short neutral alumina pad and concentrated in vacuo.

The residue (15 mg) did not contain 1,2-dibromobenzene by $^1$H NMR.

Example 3

N-Bromoamides as Reagents for Radical Bromodecarboxylation

N-Bromoamides Induced Bromodecarboxylation of 2-Bromobenzoic Acid

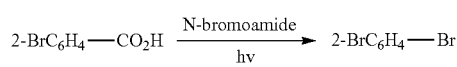

A mixture of 2-bromobenzoic acid (1 mmol), N-bromoamide, additive (optionally) and solvent (10 mL) was stirred under fluorescent room light illumination (FL). The reaction mixture was concentrated in vacuo. A solution of the residue in CDCl$_3$ was filtered directly to NMR tube. Conversion of the reaction was determined by $^1$H NMR. The results are presented in Table 2.

TABLE 2

N-Bromoamides as reagents for radical bromodecarboxylation [a]

| entry | Reaction conditions | conversion, % |
|---|---|---|
| 1 | DBI 1 mol/DCM, rt FL 24 h | 100 |
| 2 | DBI 1 mol/Br$_2$ 1 mol/DCM, rt FL 24 h | 100 |
| 3 | NBS 1 mol/DCM, rt FL 24 h | 0 |
| 4 | NBS 1 mol/Br$_2$ 1 mol/DCM, rt FL 24 h | 0 |
| 5 | DBDMH 1 mol/DCM, rt FL 24 h | 0 |
| 6 | DBDMH 1 mol/Br$_2$ 1 mol/DCM, rt FL 24 h | 6 |
| 7 | BTMH 1 mol/DCM, rt FL 24 h | 0 |
| 8 | BTMH 1 mol/Br$_2$ 1 mol/DCM, rt FL 24 h | 0 |
| 9 | BDMO 1 mol/DCM, rt FL 24 h | 0 |
| 10 | BDMO 1 mol/Br$_2$ 1 mol/DCM, rt FL 24 h | 1 |
| 11 | BPT 1 mol/DCM, rt FL 24 h | 0 |
| 12 | BPT 1 mol/Br$_2$ 1 mol/DCM, rt FL 24 h | 7 |
| 13 | BNPT 1 mol/DCM, rt FL 24 h | 0 |
| 14 | BNPT 1 mol/Br$_2$ 1 mol/DCM, rt FL 24 h | 0 |
| 15 | NBSac 1 mol/DCM, rt FL 24 h | 4 |
| 16 | NBSac 1 mol/Br$_2$ 1 mol/DCM, rt FL 24 h | 17 |

[a] All quantities in mole/mole of 2-bromobenzoic acid.

Bromodecarboxylation of 2-bromobenzoic Acid with 1,3-dibromo-5,5-dimethylhydantoin

A mixture of 2-bromobenzoic acid (0.20 g, 1 mmol), 1,3-dibromo-5,5-dimethylhydantoin DBDMH (0.29 g, 1 mmol) and 1,2-dichloroethane DCE (5 mL) was irradiated with 250 W tungsten lamp under reflux conditions for 15 h. The cooled reaction mixture was washed with 1 M aq Na$_2$SO$_3$, dried over Na$_2$SO$_4$, filtered through short neutral alumina pad and concentrated in vacuo. The residue was purified by chromatography on silica gel (eluent: hexane) to give 50 mg (20%) of 1,2-dibromobenzene.

$^1$H NMR: δ 7.65-7.59 (m, 2H), 7.19-7.14 (m, 2H) ppm.

Bromodecarboxylation of 2-bromobenzoic Acid with N-bromosuccinimide

A mixture of 2-bromobenzoic acid (0.20 g, 1 mmol), N-bromosuccinimide NBS (0.36 g, 2 mmol) and 1,2-dichloroethane DCE (5 mL) was irradiated with 250 W tungsten lamp under reflux conditions for 15 h. The cooled reaction mixture was washed with 1 M aq Na$_2$SO$_3$, dried over Na$_2$SO$_4$, filtered through short neutral alumina pad and concentrated in vacuo. The residue was purified by chromatography on silica gel (eluent: hexane) to give 10 mg (4%) of 1,2-dibromobenzene.

Example 4

Bromodecarboxylation of 2-Bromobenzoic Acid Induced by Bromoisocyanurate

Optimization of the Reaction Conditions

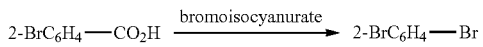

A round bottom flask equipped with Dimroth condenser (chilled to 10° C.) was charged with 2-bromobenzoic acid (1 mmol), bromoisocyanurate, additive (optionally) and solvent (10 mL). The mixture was stirred at rt or heated in an oil bath. The reaction was provided in the dark (NL) or under florescent room light irradiation (FL). The cold reaction mixture was concentrated in vacuo. The residue was dissolved in CDCl$_3$ and filtered directly to NMR tube. Conversion was determined by $^1$H NMR. The results are presented in Table 3.

TABLE 3

Bromodecarboxylation of 2-bromobenzoic acid [a]

| entry | Reaction conditions | conversion, % |
|---|---|---|
| 1 | Br$_2$ 2 mol/DCM, rt FL 24 h | 0 |
| 2 | DBI 0.5 mol/DCM, 60° FL 24 h | 30 |
| 3 | DBI 0.75 mol/DCM, 60° FL 24 h | 56 |
| 4 | DBI 1 mol/DCM, rt FL 24 h | 100 |
| 5 | DBI 1 mol/Br$_2$ 0.5 mol/DCM, rt FL 24 h | 100 |
| 6 | DBI 1 mol/Br$_2$ 1 mol/DCM, rt FL 24 h | 100 |
| 7 | DBI 1 mol/Br$_2$ 2 mol/DCM, rt FL 24 h | 100 |
| 8 | DBI 1 mol/Br$_2$ 4 mol/DCM, rt FL 24 h | 100 |
| 9 | DBI 1 mol/BrCCl$_3$, rt FL 24 h | 0 |
| 10 | DBI 1 mol/BrCCl$_3$, 120° FL 1 h | 11 |
| 11 | DBI 1 mol/Br$_2$ 2 mol/BrCCl$_3$, rt FL 24 h | 0 |
| 12 | DBI 1 mol/Br$_2$ 2 mol/BrCCl$_3$, 120° FL 1 h | 100 |
| 13 | DBI 1 mol/Br$_2$ 2 mol/BrCCl$_3$, 120° NL, 1 h | 39 |
| 14 | DBI 1 mol/Br$_2$ 2 mol/BrCCl$_3$, 120° NL 3 h | 100 |
| 15 | DBI 1 mol/CCl$_4$, 100° FL 1 h | 0 |
| 16 | DBI 1 mol/Br$_2$ 2 mol/CCl$_4$, 100° FL 6 h | 100 |
| 17 | DBI 1 mol/CHCl$_3$, rt FL 24 h | 0 |
| 18 | DBI 1 mol/DCE, rt FL 24 h | 6 |
| 19 | DBI 1 mol/PhH, rt FL 24 h | 0 |
| 20 | DBI 1 mol/PhCl, rt FL 24 h | 0 |
| 21 | DBI 1 mol/PhCF$_3$, rt F, 24 h | 0 |
| 22 | DBI 1 mol/C$_6$H$_{12}$, rt FL 24 h | 0 |
| 23 | DBI 1 mol/EtOAc, rt FL 24 h | 0 |
| 24 | DBI 1 mol/MeCN, rt FL 24 h | 33 |
| 25 | DBI 1 mol/MeNO$_2$, rt FL 24 h | 0 |

[a] All quantities in mole/mole of 2-bromobenzoic acid. Oil bath temperatures in degrees Celsius.

Example 5

Bromodecarboxylation of Arenecarboxylic Acids

Optimizing of the Reactions

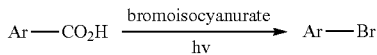

Mixture of arenecarboxylic acid (1 mmol), bromoisocyanurate, additive (optionally) and solvent (10 mL) was stirred under fluorescent room light irradiation (FL). An aliquot of the reaction mixture was concentrated in vacuo. The residue was dissolved in CDCl$_3$ and filtered directly to NMR tube. Conversion was determined by $^1$H NMR. The results are presented in Table 4.

TABLE 4

Bromodecarboxylation of arenecarboxylic acids ArCO$_2$H $^a$

| entry | ArCO$_2$H | Reaction conditions $^a$ | conversion, % |
|---|---|---|---|
| 1 | 2-NO$_2$C$_6$H$_4$CO$_2$H | DBI 1 mol/DCM, rt FL 24 h | 65 |
| 2 | 2-NO$_2$C$_6$H$_4$CO$_2$H | DBI 1 mol/Br$_2$ 1 mol/DCM, rt FL 24 h | 100 |
| 3 | 2-NO$_2$C$_6$H$_4$CO$_2$H | DBI 1 mol/Br$_2$ 2 mol/DCM, rt FL 24 h | 100 |
| 4 | 2-NO$_2$C$_6$H$_4$CO$_2$H | DBI 1 mol/Br$_2$ 3 mol/DCM, rt FL 24 h | 100 |
| 5 | 2-NO$_2$C$_6$H$_4$CO$_2$H | DBI 1 mol/Br$_2$ 4 mol/DCM, rt FL 24 h | 100 |
| 6 | 3-NO$_2$C$_6$H$_4$CO$_2$H | DBI 1 mol/DCM, rt FL 24 h | 18 |
| 7 | 3-NO$_2$C$_6$H$_4$CO$_2$H | DBI 1 mol/Br$_2$ 1 mol/DCM, rt FL 24 h | 100 |
| 8 | 3-NO$_2$C$_6$H$_4$CO$_2$H | DBI 1 mol/Br$_2$ 2 mol/DCM, rt FL 24 h | 100 |
| 9 | 3-NO$_2$C$_6$H$_4$CO$_2$H | DBI 1 mol/Br$_2$ 3 mol/DCM, rt FL 24 h | 100 |
| 10 | 3-NO$_2$C$_6$H$_4$CO$_2$H | DBI 1 mol/Br$_2$ 4 mol/DCM, rt FL 24 h | 100 |
| 11 | 4-NO$_2$C$_6$H$_4$CO$_2$H | DBI 1 mol/DCM, rt FL 24 h | 50 |
| 12 | 4-NO$_2$C$_6$H$_4$CO$_2$H | DBI 1 mol/Br$_2$ 4 mol/DCM, rt FL 24 h | 70 |
| 13 | 4-NCC$_6$H$_4$CO$_2$H | DBI 1 mol/DCM, rt FL 24 h | 55 |
| 14 | 4-NCC$_6$H$_4$CO$_2$H | DBI 1 mol/Br$_2$ 4 mol/DCM, rt FL 24 h | 85 |

$^a$ All quantities in mole/mole of arenecarboxylic acid.

Example 6

Bromoisocyanurate Induced Radical Bromodecarboxylation of Arenecarboxylic Acids

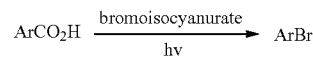

$$\text{ArCO}_2\text{H} \xrightarrow[\text{hv}]{\text{bromoisocyanurate}} \text{ArBr}$$

A mixture of arenecarboxylic acid ArCO$_2$H (1 mmol), bromoisocyanurate, additive and solvent (10 mL) was stirred under fluorescent room light (FL) or warm-white 3 W LED (LL) irradiation (hv). The reaction mixture washed with 1 M aq Na$_2$SO$_3$, dried over Na$_2$SO$_4$, filtered through short neutral alumina pad and concentrated in vacuo to yield crude bromoarene ArBr. Optionally, the crude bromide was purified by chromatography on silica gel. The results are presented in Table 5.

TABLE 5

Bromodecarboxylation of arenecarboxylic acids ArCO$_2$H $^a$

| entry | ArCO$_2$H | Reaction conditions | yield, % ArBr |
|---|---|---|---|
| 1 | 2-BrC$_6$H$_4$CO$_2$H | DBI 1 mol/Br$_2$ 1 mol/DCM, rt FL 24 h | 97 |
| 2 | 3-BrC$_6$H$_4$CO$_2$H | DBI 1 mol/Br$_2$ 1 mol/DCM, rt FL 24 h | 92 |
| 3 | 4-BrC$_6$H$_4$CO$_2$H | DBI 1 mol/Br$_2$ 1 mol/DCM, rt FL 24 h | 82 |
| 4 | 2-ClC$_6$H$_4$CO$_2$H | DBI 1 mol/Br$_2$ 1 mol/DCM, rt FL 24 h | 98 |
| 5 | 3-ClC$_6$H$_4$CO$_2$H | DBI 1 mol/Br$_2$ 1 mol/DCM, rt FL 24 h | 89 |
| 6 | 4-ClC$_6$H$_4$CO$_2$H | DBI 1 mol/Br$_2$ 1 mol/DCM, rt FL 24 h | 88 |
| 7 | 2,4-Cl$_2$C$_6$H$_3$CO$_2$H | DBI 1 mol/Br$_2$ 1 mol/DCM, rt FL 24 h | 97 |
| 8 | 2-NO$_2$C$_6$H$_4$CO$_2$H | DBI 1 mol/Br$_2$ 1 mol/DCM, rt FL 24 h | 99 |
| 9 | 3-NO$_2$C$_6$H$_4$CO$_2$H | DBI 1 mol/Br$_2$ 1 mol/DCM, rt FL 24 h | 99 |
| 10 | 4-NO$_2$C$_6$H$_4$CO$_2$H | DBI 1 mol/Br$_2$ 1 mol/DCM, rt FL 24 h | 60 |
| 11 | 3-CNC$_6$H$_4$CO$_2$H | DBI 1 mol/Br$_2$ 1 mol/DCM, rt FL 24 h | 66 |
| 12 | 4-CNC$_6$H$_4$CO$_2$H | DBI 1 mol/Br$_2$ 1 mol/DCM, rt FL 24 h | 95 |
| 13 | 2-Br-5-FC$_6$H$_3$CO$_2$H | DBI 1 mol/Br$_2$ 1 mol/DCM, rt FL 24 h | 96 |
| 14 | 5-Br-2-FC$_6$H$_3$CO$_2$H | DBI 1 mol/Br$_2$ 1 mol/DCM, rt FL 24 h | 36 |
| 15 | 5-Br-2-FC$_6$H$_3$CO$_2$H | DBI 1 mol/Br$_2$ 2 mol/DCM, 60° FL 24 h | 89 |
| 16 | 4-Cl-2-FC$_6$H$_3$CO$_2$H | DBI 1 mol/Br$_2$ 1 mol/DCM, rt FL 24 h | 60 |
| 17 | 4-NO$_2$-2-CF$_3$C$_6$H$_3$CO$_2$H | DBI 1 mol/Br$_2$ 1 mol/DCM, rt FL 24 h | 20 |
| 18 | 4-NO$_2$-2-CF$_3$C$_6$H$_3$CO$_2$H | DBI 1 mol/Br$_2$ 2 mol/DCM, 60° FL 24 h | 92 |
| 19 | 4-NO$_2$-3-CF$_3$C$_6$H$_3$CO$_2$H | DBI 1 mol/Br$_2$ 1 mol/DCM, rt FL 24 h | 45 |
| 20 | 2-MeO$_2$CC$_6$H$_4$CO$_2$H | DBI 1 mol/Br$_2$ 1 mol/DCM, rt FL 24 h | 98 |
| 21 | 3-MeO$_2$CC$_6$H$_4$CO$_2$H | DBI 1 mol/Br$_2$ 1 mol/DCM, rt FL 24 h | 98 |
| 22 | 4-MeO$_2$CC$_6$H$_4$CO$_2$H | DBI 1 mol/Br$_2$ 1 mol/DCM, rt FL 24 h | 97 |
| 23 | 3-NO$_2$-4-MeO$_2$CC$_6$H$_3$CO$_2$H | DBI 1 mol/Br$_2$ 1 mol/DCM, rt FL 24 h | 75 |
| 24 | 2-PhtNC$_6$H$_4$CO$_2$H | DBI 1 mol/Br$_2$ 1 mol/DCM, rt FL 24 h | 99 |
| 25 | trimellitic anhydride | DBI 1 mol/Br$_2$ 1 mol/DCM, rt FL 24 h | 70 |
| 26 | (t-Bu-N phthalimide-CO$_2$H structure) | DBI 1 mol/Br$_2$ 1 mol/DCM, rt FL 24 h | 71 |
| 27 | 3,5-Br$_2$C$_6$H$_3$CO$_2$H | DBI 1 mol/Br$_2$ 1 mol/DCM, rt FL 24 h | 51 (GC) |
| 28 | 3,4-F$_2$C$_6$H$_3$CO$_2$H | DBI 1 mol/Br$_2$ 2 mol/CBrCl$_3$, 120° LL 24 h | 77 (GC) |
| 29 | 2,4,5-F$_3$C$_6$H$_2$CO$_2$H | DBI 1 mol/Br$_2$ 2 mol/CBrCl$_3$, 120° LL 24 h | 95 (GC) |

TABLE 5-continued

Bromodecarboxylation of arenecarboxylic acids ArCO$_2$H $^a$

| entry | ArCO$_2$H | Reaction conditions | yield, % ArBr |
|---|---|---|---|
| 30 | 3,4,5-F$_3$C$_6$H$_2$CO$_2$H | DBI 1 mol/Br$_2$ 2 mol/CBrCl$_3$, 120° LL 24 h | 86 (GC) |
| 31 | C$_6$F$_5$CO$_2$H | DBI 1 mol/Br$_2$ 1 mol/CBrCl$_3$, 120° LL 24 h | 70 (GC) |

$^a$ All quantities in mole/mole of arenecarboxylic acid. Oil bath temperatures in degrees Celsius.

Entry 1: 1,2-Dibromobenzene $^1$H NMR: δ 7.62 (dd, J=6, 4 Hz, 2H), 7.16 (dd, J=6, 4 Hz, 2H) ppm; $^{13}$C NMR: δ 133.9, 128.6, 124.9 ppm.

Entry 2: 1,3-Dibromobenzene $^1$H NMR: δ 7.67 (t, J=2 Hz, 1H), 7.43 (dd, J=8, 2 Hz, 2H), 7.1 (t, J=8 Hz, 1H) ppm; $^{13}$C NMR: δ 134.3, 131.2, 130.3, 123.1 ppm.

Entry 3: 1,4-Dibromobenzene $^1$H NMR: δ 7.35 (s, 4H) ppm; $^{13}$C NMR: δ 133.2, 121.1 ppm.

Entry 4: 1-Bromo-2-chlorobenzene $^1$H NMR: δ 7.61 (dd, J=8, 1.4 Hz, 1H), 7.45 (dd, J=8, 1.4 Hz, 1H), 7.24 (td, J=8, 1.4 Hz, 1H), 7.11 (td, J=8, 1.4 Hz, 1H) ppm; $^{13}$C NMR: δ 134.6, 133.9, 130.5, 128.5, 127.9, 122.6 ppm.

Entry 5: 1-Bromo-3-chlorobenzene $^1$H NMR: δ 7.52 (t, J=2 Hz, 1H), 7.39 (d, J=8 Hz, 1H), 7.28 (d, J=8 Hz, 1H), 7.16 (t, J=8 Hz, 1H) ppm; $^{13}$C NMR: δ 135.3, 131.6, 130.9, 129.9, 127.4, 122.9 ppm.

Entry 6: 1-Bromo-4-chlorobenzene $^1$H NMR: δ 7.42 (dt, J=9, 3 Hz, 2H), 7.10-7.22 (m, 2H) ppm; $^{13}$C NMR: δ 133.3, 132.9, 130.3, 120.4 ppm.

Entry 7: 1-Bromo-2,4-dichlorobenzene $^1$H NMR: δ 7.52 (d, J=9 Hz, 1H), 7.45 (d, J=2 Hz, 1H), 7.10 (dd, J=9, 2 Hz, 1H) ppm; $^{13}$C NMR: δ 135.5, 134.4, 133.9, 130.3, 128.3, 120.8 ppm.

Entry 8: 1-Bromo-2-nitrobenzene $^1$H NMR: δ 7.84 (dd, J=8, 2 Hz, 1H), 7.74 (dd, J=8, 2 Hz, 1H), 7.49-7.40 (m, 2H) ppm; $^{13}$C NMR: δ 150.1, 135.2, 133.3, 128.3, 125.7, 114.6 ppm.

Entry 9: 1-Bromo-3-nitrobenzene $^1$H NMR: δ 8.38 (t, J=1 Hz, 1H), 8.17 (dd, J=8, 1 Hz, 1H), 7.83 (dd, J=8, 1 Hz, 1H), 7.44 (t, J=8 Hz, 1H) ppm; $^{13}$C NMR: δ 148.9, 137.7, 130.7, 126.9, 123.0, 122.2 ppm.

Entry 10: 1-Bromo-4-nitrobenzene $^1$H NMR: δ 8.08 (d, J=9 Hz, 2H), 7.67 (d, J=9 Hz, 2H) ppm; $^{13}$C NMR: δ 147.1, 132.7, 130.1, 125.1 ppm.

Entry 11: 3-Bromobenzonitrile $^1$H NMR: δ 7.79 (s, 1H), 7.74 (d, J=8 Hz, 1H), 7.60 (d, J=8 Hz, 1H), 7.36 (t, J=8 Hz, 1H) ppm; $^{13}$C NMR: δ 136.2, 134.9, 130.8, 130.7, 123.0, 117.4, 114.3 ppm.

Entry 12: 4-Bromobenzonitrile $^1$H NMR: δ 7.63 (d, J=9 Hz, 2H), 7.52 (d, J=9 Hz, 2H) ppm; $^{13}$C NMR: δ 133.5, 132.7, 128.1, 118.1, 111.4 ppm.

Entry 13: 1,2-Dibromo-4-fluorobenzene $^1$H NMR: δ 7.57 (dd, J=9, 6 Hz, 1H), 7.37 (dd, J=8, 3 Hz, 1H), 6.29 (td, J=6, 39 Hz, 1H) ppm; $^{13}$C NMR: δ 161.5 (d, $J_{CF}$=251 Hz), 134.4 (d, $J_{CF}$=9 Hz), 125.3 (d, $J_{CF}$=10 Hz), 121.3, 121.1, 119.7 (d, $J_{CF}$=4 Hz) ppm.

Entries 14-15: 2,4-Dibromo-1-fluorobenzene $^1$H NMR: δ 7.69 (dd, J=6, 2 Hz, 1H), 7.39 (ddd, J=9, 4, 2 Hz, 1H), 7.01 (t, J=9 Hz, 1H) ppm; $^{13}$C NMR: δ 158.5 (d, $J_{CF}$=248 Hz), 136.0, 132.1 (d, $J_{CF}$=7 Hz), 117.9 (d, $J_{CF}$=24 Hz), 117.1 (d, $J_{CF}$=4 Hz), 110.3 (d, $J_{CF}$=22 Hz), ppm.

Entry 16: 1-Bromo-4-chloro-2-fluorobenzene $^1$H NMR: δ 7.47 (t, J=8 Hz, 1H), 7.15 (dd, J=8, 2 Hz, 1H), 7.04 (d, J=8 Hz, 1H) ppm; $^{13}$C NMR: δ 159.1 (d, $J_{CF}$=250 Hz), 134.1, 125.8 (d, $J_{CF}$=4 Hz), 117.0 (d, $J_{CF}$=25 Hz), 107.4 (d, $J_{CF}$=21 Hz) ppm.

Entry 17-18: 1-Bromo-4-nitro-2-(trifluoromethyl)benzene $^1$H NMR: δ 8.50 (d, J=2 Hz, 1H), 8.26 (dd, J=9, 2 Hz, 1H), 7.96 (d, J=9 Hz, 1H) ppm; $^{13}$C NMR: δ 146.9, 136.5, 131.8 (d, $J_{CF}$=33 Hz), 127.7, 127.5, 123.2 (q, $J_{CF}$=6 Hz), 122.0 (q, $J_{CF}$=274 Hz) ppm; $^{19}$F NMR: δ −66.4 ppm.

Entry 19: 4-Bromo-1-nitro-2-(trifluoromethyl)benzene $^1$H NMR: δ 7.97 (d, J=2 Hz, 1H), 7.87 (dd, J=9, 2 Hz, 1H), 7.80 (d, J=9 Hz, 1H) ppm; $^{13}$C NMR: δ 147.0, 136.3, 131.4 (q, $J_{CF}$=11, 5 Hz), 127.4, 126.7, 125.5 (d, $J_{CF}$=35 Hz), 121.2 (q, $J_{CF}$=274 Hz) ppm; $^{19}$F NMR: δ −63.3 ppm.

Entry 20: Methyl 2-bromobenzoate $^1$H NMR: δ 7.74 (d, J=8 Hz, 1H), 7.60 (d, J=8 Hz, 1H), 7.34-7.24 (m, 2H), 3.88 (s, 3H) ppm; $^{13}$C NMR: δ 166.5, 134.3, 132.5, 132.1, 131.2, 127.1, 121.6, 52.4 ppm.

Entry 21: Methyl 3-bromobenzoate $^1$H NMR: δ 8.16 (s, 1H), 7.95 (d, J=8 Hz, 1H), 7.66 (d, J=8 Hz, 1H), 7.30 (t, J=8 Hz, 3H), 3.91 (s, 3H) ppm; $^{13}$C NMR: δ 165.8, 135.9, 132.7, 132.1, 130.0, 128.2, 122.5, 55.5 ppm Entry 22: Methyl 4-bromobenzoate $^1$H NMR: δ 7.89 (d, J=8 Hz, 2H), 7.57 (d, J=8 Hz, 2H), 3.91 (s, 3H) ppm; $^{13}$C NMR: δ 166.5, 131.8, 131.2, 129.1, 128.1, 52.4 ppm.

Entry 23: Methyl 4-bromo-2-nitrobenzoate $^1$H NMR: δ 8.00 (d, J=2 Hz, 1H), 7.79 (dd, J=8, 2 Hz, 1H), 7.64 (d, J=2 Hz, 1H), 3.90 (s, 3H) ppm; $^{13}$C NMR: δ 164.9, 149.0, 135.9, 131.4, 127.1, 125.9, 125.8, 53.5 ppm.

Entry 24: 1-Bromo-2-phthalimidobenzene $^1$H NMR: δ 8.00-7.95 (m, 2H), 7.84-7.78 (m, 2H), 7.74 (dd, J=8, 1 Hz, 1H), 7.47 (dt, J=8, 1 Hz, 1H), 7.40-7.32 (m, 2H) ppm; $^{13}$C NMR: δ 166.7, 134.6, 133.7, 132.0, 131.5, 131.0, 130.9, 128.5, 124.1, 123.4 ppm;

Entry 25: 4-Bromophthalic anhydride $^1$H NMR: δ 8.16 (d, J=1 Hz, 1H), 8.04 (dd, J=8, 1 Hz, 1H), 7.88 (d, J=8 Hz, 1H) ppm; $^{13}$C NMR: δ 161.9, 161.5, 139.4, 133.0, 131.6, 129.9, 129.0, 127.0 ppm.

Entry 26: N-(tert-Butyl)-4-bromophthalimide $^1$H NMR: δ 7.88 (d, J=1 Hz, 1H), 7.80 (dd, J=8, 1 Hz, 1H), 7.62 (d, J=8 Hz, 1H), 1.68 (s, 3H) ppm; $^{13}$C NMR: δ 168.9, 168.3, 136.8, 133.9, 130.8, 128.6, 126.1, 124.2, 58.3, 29.1 ppm.

Example 7

Bromodecarboxylation of Arenedicarboxylic Acids Induced by Bromoisocyanurate

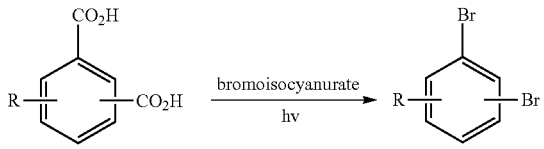

Round bottom flask equipped with Dimroth condenser (chilled to 10° C.) was charged with arenedicarboxylic acid RC$_6$H$_3$(CO$_2$H)$_2$ (1 mmol), bromoisocyanurate, additive and solvent (10 mL). The mixture was magnetically stirred and heated in an oil bath at 120° C. under florescent room light irradiation (FL) for 60 h. The cooled reaction mixture was filtered through short silica gel pad, washed with 1 M aq $Na_2SO_3$, dried over $Na_2SO_4$, filtered and concentrated in vacuo to give crude dibromoarene $RC_6H_3Br_2$. Optionally, the crude dibromide was purified by chromatography on silica gel. The results are presented in Table 6.

TABLE 6

Bromodecarboxylation of arenedicarboxylic acids $RC_6H_3(CO_2H)_2$ [a]

| entry | $RC_6H_3(CO_2H)_2$ | Reaction conditions | Yield, % $RC_6H_3Br_2$ |
|---|---|---|---|
| 1 | 4-$NO_2$-1,2-$C_6H_3(CO_2H)_2$ | DBI 2 mol/$Br_2$ 2 mol/$BrCCl_3$, 120° FL 2 h | 32 |
| 2 | 1,3-$C_6H_4(CO_2H)_2$ | DBI 2 mol/$Br_2$ 2 mol/$BrCCl_3$, 120° FL 2 h | 6 |
| 3 | 1,3-$C_6H_4(CO_2H)_2$ | DBI 2 mol/$Br_2$ 2 mol/$BrCCl_3$, 120° FL 24 h | 12 |
| 4 | 1,3-$C_6H_4(CO_2H)_2$ | DBI 2 mol/$Br_2$ 2 mol/$BrCCl_3$, 120° FL 60 h | 17 |
| 5 | 5-$NO_2$-1,3-$C_6H_3(CO_2H)_2$ | DBI 2 mol/$Br_2$ 2 mol/$BrCCl_3$, 120° FL 2 h | 17 |
| 6 | 5-$NO_2$-1,3-$C_6H_3(CO_2H)_2$ | DBI 2 mol/$Br_2$ 2 mol/$BrCCl_3$, 120° FL 24 h | 20 |
| 7 | 5-$NO_2$-1,3-$C_6H_3(CO_2H)_2$ | DBI 2 mol/$Br_2$ 2 mol/$BrCCl_3$, 120° FL 60 h | 25 |
| 8 | 1,4-$C_6H_4(CO_2H)_2$ | DBI 2 mol/$Br_2$ 2 mol/$BrCCl_3$, 120° FL 2 h | 12 |

[a] All quantities in mole/mole of arenedicarboxylic acid. Oil bath temperatures in degrees Celsius.

Example 8

Bromoisocyanurate Induced Radical Bromodecarboxylation of Alkanoic Acids

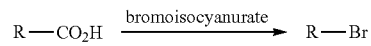

Bromodecarboxylation of Lauric Acid: Optimization of the Reaction Conditions

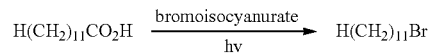

A mixture of lauric acid (0.5 mmol), bromoisocyanurate, additive (optionally), and DCM (4 mL) was stirred under fluorescent room light (FL) or warm-white 3 W LED lamp irradiation (LL), or in the dark (NL). An aliquot of the reaction mixture washed with 1 M aq $Na_2SO_3$, dried over $Na_2SO_4$, and filtered through short neutral silica gel pad. The yield of 1-bromoundecane was determined by gas chromatography (GC) using 1,2,4,5-tetrachlorobenzene as internal standard. The results are presented in Table 7.

TABLE 7

Bromodecarboxylation of lauric acid [a]

| entry | Reaction conditions | yield, % [b] |
|---|---|---|
| 1 | DBI 1 mol/DCM, rt FL 1 h | 0 |
| 2 | DBI 1 mol/DCM, rt FL 4 h | 0 |
| 3 | DBI 1 mol/DCM, rt FL 21 h | 58 |
| 4 | DBI 1 mol/$Br_2$ 0.1 mol/DCM, rt FL 1 h | 8 |
| 5 | DBI 1 mol/$Br_2$ 0.1 mol/DCM, rt FL 2 h | 17 |
| 6 | DBI 1 mol/$Br_2$ 0.1 mol/DCM, rt FL 3 h | 24 |
| 7 | DBI 1 mol/$Br_2$ 0.1 mol/DCM, rt FL 4 h | 31 |
| 8 | DBI 1 mol/$Br_2$ 0.2 mol/DCM, rt FL 1 h | 20 |
| 9 | DBI 1 mol/$Br_2$ 0.2 mol/DCM, rt FL 2 h | 39 |
| 10 | DBI 1 mol/$Br_2$ 0.2 mol/DCM, rt FL 3 h | 62 |
| 11 | DBI 1 mol/$Br_2$ 0.2 mol/DCM, rt FL 4 h | 79 |
| 12 | DBI 1 mol/$Br_2$ 0.2 mol/DCM, rt FL 5 h | 79 |
| 13 | DBI 1 mol/$Br_2$ 0.3 mol/DCM, rt FL 1 h | 25 |
| 14 | DBI 1 mol/$Br_2$ 0.3 mol/DCM, rt FL 2 h | 51 |
| 15 | DBI 1 mol/$Br_2$ 0.3 mol/DCM, rt FL 3 h | 72 |
| 16 | DBI 1 mol/$Br_2$ 0.3 mol/DCM, rt FL 4 h | 83 |
| 17 | DBI 1 mol/$Br_2$ 0.3 mol/DCM, rt FL 5 h | 80 |
| 18 | DBI 1 mol/$Br_2$ 0.4 mol/DCM, rt FL 1 h | 23 |
| 19 | DBI 1 mol/$Br_2$ 0.4 mol/DCM, rt FL 2 h | 50 |
| 20 | DBI 1 mol/$Br_2$ 04 mol/DCM, rt FL 3 h | 70 |
| 21 | DBI 1 mol/$Br_2$ 0.4 mol/DCM, rt FL 4 h | 80 |
| 22 | DBI 1 mol/$Br_2$ 0.5 mol/DCM, rt FL 1 h | 36 |
| 23 | DBI 1 mol/$Br_2$ 0.5 mol/DCM, rt FL 2 h | 70 |
| 24 | DBI 1 mol/$Br_2$ 0.5 mol/DCM, rt FL 3 h | 82 |
| 25 | DBI 1 mol/$Br_2$ 0.5 mol/DCM, rt FL 4 h | 71 |
| 26 | DBI 1 mol/$Br_2$ 1 mol/DCM, rt FL 1 h | 43 |
| 27 | DBI 1 mol/$Br_2$ 1 mol/DCM, rt FL 2 h | 73 |
| 28 | DBI 1 mol/$Br_2$ 1 mol/DCM, rt FL 3 h | 70 |
| 29 | DBI 1 mol/$Br_2$ 1 mol/DCM, rt FL 4 h | 60 |
| 30 | DBI 1 mol/$Br_2$ 2 mol/DCM, rt FL 1 h | 55 |
| 31 | DBI 1 mol/$Br_2$ 2 mol/DCM, rt FL 2 h | 78 |
| 32 | DBI 1 mol/$Br_2$ 2 mol/DCM, rt FL 3 h | 70 |
| 33 | DBI 1 mol/$Br_2$ 0.3 mol/DCM, rt NL 2 h | 1 |
| 34 | DBI 1 mol/$Br_2$ 0.3 mol/DCM, rt NL 4 h | 2 |
| 35 | DBI 1 mol/$Br_2$ 0.3 mol/DCM, rt NL 8 h | 3 |
| 36 | DBI 1 mol/$Br_2$ 0.3 mol/DCM, rt NL 24 h | 4 |

TABLE 7-continued

Bromodecarboxylation of lauric acid [a]

| entry | Reaction conditions | yield, % [b] |
|---|---|---|
| 37 | DBI 1 mol/Br$_2$ 0.3 mol/DCM, 3° FL 2 h | 8 |
| 38 | DBI 1 mol/Br$_2$ 0.3 mol/DCM, 3° FL 4 h | 19 |
| 39 | DBI 1 mol/Br$_2$ 0.3 mol/DCM, 3° FL 8 h | 41 |
| 40 | DBI 1 mol/Br$_2$ 0.3 mol/DCM, 3° FL 24 h | 79 |
| 41 | DBI 1 mol/I$_2$ 0.3 mol/DCM, rt FL 1 h | 0 |
| 42 | DBI 1 mol/I$_2$ 0.3 mol/DCM, rt FL 2 h | 9 |
| 43 | DBI 1 mol/I$_2$ 0.3 mol/DCM, rt FL 5.5 h | 31 |
| 44 | DBI 1 mol/I$_2$ 0.3 mol/DCM, rt FL 19 h | 35 |
| 45 | DBI 1 mol/[NBu$_4$]Br$_3$ 0.3 mol/DCM, rt FL 1 h | 25 |
| 46 | DBI 1 mol/[NBu$_4$]Br$_3$ 0.3 mol/DCM, rt FL 2 h | 62 |
| 47 | DBI 1 mol/[NBu$_4$]Br$_3$ 0.3 mol/DCM, rt FL 3 h | 84 |
| 48 | DBI 1 mol/[NBu$_4$]Br$_3$ 0.3 mol/DCM, rt FL 4 h | 98 |
| 49 | DBI 1 mol/[NBu$_4$]Br$_3$ 0.3 mol/DCM, rt FL 5 h | 96 |
| 50 | DBI 1 mol/[NBu$_4$]Br$_3$ 0.3 mol/DCM, rt FL 20 h | 71 |
| 51 | DBI 1 mol/[NBu$_4$]Br$_3$ 0.1 mol/DCM, rt FL 4 h | 78 |
| 52 | DBI 1 mol/[NBu$_4$]Br$_3$ 0.1 mol/DCM, rt FL 5 h | 92 |
| 53 | DBI 1 mol/[NBu$_4$]Br$_3$ 0.1 mol/DCM, rt FL 6 h | 95 |
| 54 | DBI 1 mol/[NBu$_4$]Br$_3$ 0.3 mol/TEMPO 0.1 mol/DCM, rt FL 1 h | 0 |
| 55 | DBI 1 mol/[NBu$_4$]Br$_3$ 0.3 mol/TEMPO 0.1 mol/DCM, rt FL 2 h | 0 |
| 56 | DBI 1 mol/[NBu$_4$]Br$_3$ 0.3 mol/TEMPO 0.1 mol/DCM, rt FL 4 h | 1 |
| 57 | DBI 1 mol/[NBu$_4$]Br$_3$ 0.3 mol/DCM, rt LL 1 h | 82 |
| 58 | DBI 1 mol/[NBu$_4$]Br$_3$ 0.3 mol/DCM, rt LL 2 h | 66 |
| 59 | DBI 1 mol/[NBu$_4$]Br$_3$ 0.3 mol/DCM, 0° LL 1 h | 67 |
| 60 | DBI 1 mol/[NBu$_4$]Br$_3$ 0.3 mol/DCM, 0° LL 2 h | 93 |
| 61 | DBI 1 mol/[NBu$_4$]Br$_3$ 0.3 mol/DCM, 0° LL 3 h | 100 |
| 62 | DBI 1 mol/[NBu$_4$]Br$_3$ 0.3 mol/DCM, 0° LL 4 h | 95 |
| 63 | DBI 0.5 mol/[NBu$_4$]Br$_3$ 0.3 mol/DCM, 0° LL 1 h | 40 |
| 64 | DBI 0.5 mol/[NBu$_4$]Br$_3$ 0.3 mol/DCM, 0° LL 2 h | 70 |
| 65 | DBI 0.5 mol/[NBu$_4$]Br$_3$ 0.3 mol/DCM, 0° LL 3 h | 78 |
| 66 | DBI 0.5 mol/[NBu$_4$]Br$_3$ 0.3 mol/DCM, 0° LL 4 h | 79 |
| 67 | DBI 1 mol/[NBu$_4$]Br$_3$ 0.3 mol/DCM, −20° LL 1 h | 5 |
| 68 | DBI 1 mol/[NBu$_4$]Br$_3$ 0.3 mol/DCM, −20° LL 2 h | 11 |
| 69 | DBI 1 mol/[NBu$_4$]Br$_3$ 0.3 mol/DCM, −20° LL 3 h | 15 |
| 70 | DBI 1 mol/[NEt$_4$]Br$_3$ 0.3 mol/Br$_2$ 0.3 mol/DCM, rt FL 1 h | 11 |
| 71 | DBI 1 mol/[NEt$_4$]Br$_3$ 0.3 mol/Br$_2$ 0.3 mol/DCM, rt FL 2 h | 25 |
| 72 | DBI 1 mol/[NEt$_4$]Br$_3$ 0.3 mol/Br$_2$ 0.3 mol/DCM, rt FL 4 h | 54 |
| 73 | DBI 1 mol/[NEt$_4$]Br$_3$ 0.3 mol/Br$_2$ 0.3 mol/DCM, rt FL 6 h | 83 |
| 74 | DBI 1 mol/[NEt$_4$]Br$_3$ 0.3 mol/DCM, rt FL 1 h | 18 |
| 75 | DBI 1 mol/[NEt$_4$]Br$_3$ 0.3 mol/DCM, rt FL 4 h | 68 |
| 76 | DBI 1 mol/[NEt$_4$]Br$_3$ 0.3 mol/DCM, rt FL 6 h | 94 |
| 77 | DBI 1 mol/[N(C$_6$H$_{13}$)$_4$]Br 0.3 mol/Br$_2$ 0.3 mol/DCM, rt FL 1 h | 16 |
| 78 | DBI 1 mol/[N(C$_6$H$_{13}$)$_4$]Br 0.3 mol/Br$_2$ 0.3 mol/DCM, rt FL 4 h | 67 |
| 79 | DBI 1 mol/[N(C$_6$H$_{13}$)$_4$]Br 0.3 mol/Br$_2$ 0.3 mol/DCM, rt FL 6 h | 85 |
| 80 | DBI 1 mol/[BuNEt$_3$]Br 0.3 mol/Br$_2$ 0.3 mol/DCM, 0° LL 1 h | 41 |
| 81 | DBI 1 mol/[BuNEt$_3$]Br 0.3 mol/Br$_2$ 0.3 mol/DCM, 0° LL 2 h | 77 |
| 82 | DBI 1 mol/[BuNEt$_3$]Br 0.3 mol/Br$_2$ 0.3 mol/DCM, 0° LL 3 h | 95 |
| 83 | DBI 1 mol/[BuNEt$_3$]Br 0.3 mol/Br$_2$ 0.3 mol/DCM, 0° LL 4 h | 100 |
| 84 | DBI 1 mol/[MeN(C$_8$H$_{17}$)$_3$]Br 0.3 mol/Br$_2$ 0.3 mol/DCM, rt FL 1 h | 9 |
| 85 | DBI 1 mol/[MeN(C$_8$H$_{17}$)$_3$]Br 0.3 mol/Br$_2$ 0.3 mol/DCM, rt FL 2 h | 22 |
| 86 | DBI 1 mol/[MeN(C$_8$H$_{17}$)$_3$]Br 0.3 mol/Br$_2$ 0.3 mol/DCM, rt FL 4 h | 48 |
| 87 | DBI 1 mol/[MeN(C$_8$H$_{17}$)$_3$]Br 0.3 mol/Br$_2$ 0.3 mol/DCM, rt FL 6 h | 72 |
| 88 | DBI 1 mol/[PhNMe$_3$]Br$_3$ 0.3 mol/DCM, rt FL 4 h | 79 |
| 89 | DBI 1 mol/[PhCH$_2$NMe$_3$]Br$_3$ 0.3 mol/DCM, rt FL 1 h | 8 |
| 90 | DBI 1 mol/[PhCH$_2$NMe$_3$]Br$_3$ 0.3 mol/DCM, rt FL 4 h | 83 |
| 91 | DBI 1 mol/[PhCH$_2$NMe$_3$]Br$_3$ 0.3 mol/DCM, rt FL 6 h | 89 |
| 92 | DBI 1 mol/[C$_5$H$_5$NH]Br$_3$ 0.3 mol/DCM, rt FL 4 h | 76 |
| 93 | DBI 1 mol/[DBUH]Br$_3$ 0.3 mol/DCM, 0° LL 1 h | 57 |
| 94 | DBI 1 mol/[DBUH]Br$_3$ 0.3 mol/DCM, 0° LL 2 h | 86 |
| 95 | DBI 1 mol/[DBUH]Br$_3$ 0.3 mol/DCM, 0° LL 3 h | 94 |
| 96 | DBI 1 mol/[PBu$_4$]Br 0.3 mol/Br$_2$ 0.3 mol/DCM, rt FL 1 h | 19 |
| 97 | DBI 1 mol/[PBu$_4$]Br 0.3 mol/Br$_2$ 0.3 mol/DCM, rt FL 4 h | 87 |
| 98 | DBI 1 mol/[PBu$_4$]Br 0.3 mol/Br$_2$ 0.3 mol/DCM, rt FL 6 h | 81 |
| 99 | DBI 1 mol/ 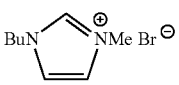 0.3 mol/Br$_2$ 0.3 mol/DCM, 0° LL 1 h | 36 |
| 100 | DBI 1 mol/ 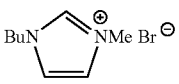 0.3 mol/Br$_2$ 0.3 mol/DCM, 0° LL 2 h | 73 |

TABLE 7-continued

Bromodecarboxylation of lauric acid [a]

| entry | Reaction conditions | yield, % [b] |
|---|---|---|
| 101 | DBI 1 mol/ BuN⊕=NMe Br⊖ 0.3 mol/Br$_2$ 0.3 mol/DCM, 0° LL 3 h | 95 |
| 102 | DBI 1 mol/ BuN⊕=NMe Br⊖ 0.3 mol/Br$_2$ 0.3 mol/DCM, 0° LL 4 h | 100 |
| 103 | DBI 1 mol/ pyrrolidinium Bu/Me Br⊖ 0.3 mol/Br$_2$ 0.3 mol/DCM, 0° LL 1 h | 40 |
| 104 | DBI 1 mol/ pyrrolidinium Bu/Me Br⊖ 0.3 mol/Br$_2$ 0.3 mol/DCM, 0° LL 4 h | 95 |

[a] All quantities in mole/mole of lauric acid. Water/ice/salt bath temperatures in degrees Celsius.
[b] 1-Bromoundecane analyzed by GC.

Example 9

Bromodecarboxylation of Cyclohexanecarboxylic Acid Optimization of the Reaction Conditions

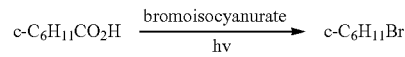

$$c\text{-}C_6H_{11}CO_2H \xrightarrow[hv]{\text{bromoisocyanurate}} c\text{-}C_6H_{11}Br$$

A mixture of cyclohexanecarboxylic acid (0.5 mmol), bromoisocyanurate, additive (optionally) and solvent (4 mL) was stirred under fluorescent room light irradiation (FL). An aliquot of the reaction mixture washed with 1 M aq Na$_2$SO$_3$, dried over Na$_2$SO$_4$, and filtered through short neutral silica gel pad. The yield of bromocyclohexane was determined by gas chromatography (GC) using 1,2,4,5-tetrachlorobenzene as internal standard. The results are presented in Table 8.

TABLE 8

Bromodecarboxylation of cyclohexanecarboxylic acid [a]

| entry | Reaction conditions | yield % [b] |
|---|---|---|
| 1 | DBI 1 mol/Br$_2$ 0.2 mol/DCM, rt FL 1 h | 10 |
| 2 | DBI 1 mol/Br$_2$ 0.2 mol/DCM, rt FL 2 h | 23 |
| 3 | DBI 1 mol/Br$_2$ 0.2 mol/DCM, rt FL 3 h | 35 |
| 4 | DBI 1 mol/Br$_2$ 0.2 mol/DCM, rt FL 4 h | 43 |
| 5 | DBI 1 mol/Br$_2$ 0.3 mol/DCM, rt FL 1 h | 23 |
| 6 | DBI 1 mol/Br$_2$ 0.3 mol/DCM, rt FL 2 h | 47 |
| 7 | DBI 1 mol/Br$_2$ 0.3 mol/DCM, rt FL 3 h | 70 |
| 8 | DBI 1 mol/Br$_2$ 0.3 mol/DCM, rt FL 4 h | 62 |
| 9 | DBI 1 mol/Br$_2$ 0.4 mol/DCM, rt FL 1 h | 23 |
| 10 | DBI 1 mol/Br$_2$ 0.4 mol/DCM, rt FL 2 h | 49 |
| 11 | DBI 1 mol/Br$_2$ 0.4 mol/DCM, rt FL 3 h | 55 |
| 12 | DBI 1 mol/Br$_2$ 0.4 mol/DCM, rt FL 4 h | 51 |

[a] All quantities in mole/mole of cyclohexanecarboxylic acid.
[b] Bromocyclohexane analyzed by GC.

Example 10

Bromodecarboxylation of 2-methylcaproic Acid Optimization of the Reaction Conditions

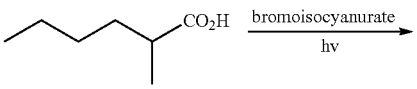

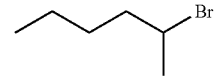

A mixture of 2-methylcaproic acid (0.5 mmol), bromoisocyanurate, additive (optionally) and solvent (4 mL) was stirred under fluorescent room light irradiation (FL). An aliquot of the reaction mixture washed with 1 M aq Na$_2$SO$_3$, dried over Na$_2$SO$_4$, and filtered through short neutral silica gel pad. The yield of 2-bromohexane was determined by gas chromatography (GC) using 1,2,4,5-tetrachlorobenzene as internal standard. The results are presented in Table 9.

TABLE 9

Bromodecarboxylation of 2-methylcaproic acid [a]

| entry | Reaction conditions | yield % [b] |
|---|---|---|
| 1 | DBI 1 mol/[NBu$_4$]Br$_3$ 0.1 mol/DCM, rt FL 1 h | 10 |
| 2 | DBI 1 mol/[NBu$_4$]Br$_3$ 0.1 mol/DCM, rt FL 3 h | 34 |
| 3 | DBI 1 mol/[NBu$_4$]Br$_3$ 0.1 mol/DCM, rt FL 5 h | 59 |
| 4 | DBI 1 mol/[NBu$_4$]Br$_3$ 0.1 mol/DCM, rt FL 19 h | 72 |
| 5 | DBI 1 mol/[NBu$_4$]Br$_3$ 0.3 mol/DCM, rt FL 1 h | 19 |
| 6 | DBI 1 mol/[NBu$_4$]Br$_3$ 0.3 mol/DCM, rt FL 3 h | 59 |
| 7 | DBI 1 mol/[NBu$_4$]Br$_3$ 0.3 mol/DCM, rt FL 5 h | 79 |
| 8 | DBI 1 mol/[NBu$_4$]Br$_3$ 0.3 mol/DCM, rt FL 7 h | 73 |
| 9 | DBI 1 mol/[NBu$_4$]Br$_3$ 0.5 mol/DCM, rt FL 1 h | 33 |
| 10 | DBI 1 mol/[NBu$_4$]Br$_3$ 0.5 mol/DCM, rt FL 2 h | 67 |
| 11 | DBI 1 mol/[NBu$_4$]Br$_3$ 0.5 mol/DCM, rt FL 3 h | 87 |
| 12 | DBI 1 mol/[NBu$_4$]Br$_3$ 0.5 mol/DCM, rt FL 4 h | 85 |
| 13 | DBI 1 mol/[NBu$_4$]Br$_3$ 0.7 mol/DCM, rt FL 1 h | 33 |

TABLE 9-continued

Bromodecarboxylation of 2-methylcaproic acid [a]

| entry | Reaction conditions | yield % [b] |
|---|---|---|
| 14 | DBI 1 mol/[NBu$_4$]Br$_3$ 0.7 mol/DCM, rt FL 3 h | 88 |
| 15 | DBI 1 mol/[NBu$_4$]Br$_3$ 0.7 mol/DCM, rt FL 4 h | 86 |

[a] All quantities in mole/mole of 2-methylcaproic acid.
[b] 2-Bromohexane analyzed by GC.

Example 11

Bromodecarboxylation of 4-Chlorophenylacetic Acid Optimization of the Reaction Conditions

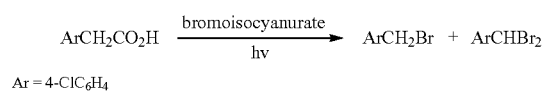

Ar = 4-ClC$_6$H$_4$

A mixture of 4-chlorophenylacetic acid ArCH$_2$CO$_2$H (Ar=4-ClC$_6$H$_4$) (1 mmol), bromoisocyanurate, additive (optionally) and solvent (6 mL) was stirred under fluorescent room light irradiation (FL). An aliquot of the reaction mixture was washed with 1 M aq Na$_2$SO$_3$, dried over Na$_2$SO$_4$, and filtered through short neutral silica gel pad. The yields of 4-chlorobenzyl bromide ArCH$_2$Br and 4-chlorobenzal bromide ArCHBr$_2$ were determined by gas chromatography (GC) using 1,2,4-trichlorobenzene as internal standard. The results are presented in Table 10.

TABLE 10

Bromodecarboxylation of 4-chlorophenylacetic acid ArCH$_2$CO$_2$H (Ar = 4-ClC$_6$H$_4$)[a]

| entry | Reaction conditions | GC yield, % ArCH$_2$Br/ ArCHBr$_2$ |
|---|---|---|
| 1 | DBI 1 mol/Br$_2$ 0.3 mol/DCM, FL rt 0.5 h | 8:5 |
| 2 | DBI 1 mol/Br$_2$ 0.3 mol/DCM, FL rt 1 h | 7:13 |
| 3 | DBI 1 mol/Br$_2$ 0.3 mol/DCM, FL rt 2 h | 4:23 |
| 4 | DBI 1 mol/[NBu$_4$]Br 0.5 mol/DCM, FL rt 1 h | 36:0 |
| 5 | DBI 1 mol/[NBu$_4$]Br 0.5 mol/DCM, FL rt 2 h | 66:0 |
| 6 | DBI 1 mol/[NBu$_4$]Br 0.5 mol/DCM, FL rt 3 h | 67:0 |
| 7 | DBI 1 mol/[NBu$_4$]Br 0.5 mol/DCM, FL rt 22 h | 53:0 |
| 8 | DBI 1 mol/[NBu$_4$]Br 0.5 mol/Br$_2$ 0.5 mol/DCM, FL rt 1 h | 82:0 |
| 9 | DBI 1 mol/[NBu$_4$]Br 0.5 mol/Br$_2$ 0.5 mol/DCM, FL rt 2 h | 83:1 |
| 10 | DBI 1 mol/[NBu$_4$]Br$_3$ 0.5 mol/DCM, FL rt 1 h | 92:0 |
| 11 | DBI 1 mol/[NBu$_4$]Br$_3$ 0.5 mol/DCM, FL rt 2 h | 92:1 |
| 12 | DBI 1 mol/[NBu$_4$]Br$_3$ 0.5 mol/DCM, FL rt 3 days | 68:8 |
| 13 | DBI 1 mol/[NBu$_4$]Br$_3$ 0.3 mol/DCM, FL rt 1 h | 95:0 |
| 14 | DBI 1 mol/[NBu$_4$]Br$_3$ 0.3 mol/DCM, FL rt 2 h | 94:2 |
| 15 | DBI 1 mol/[NBu$_4$]Br$_3$ 0.2 mol/DCM, FL rt 1 h | 79:0 |
| 16 | DBI 1 mol/[NBu$_4$]Br$_3$ 0.2 mol/DCM, FL rt 2 h | 93:2 |
| 17 | DBI 1 mol/[NBu$_4$]Br$_3$ 0.1 mol/DCM, FL rt 1 h | 59:0 |
| 18 | DBI 1 mol/[NBu$_4$]Br$_3$ 0.1 mol/DCM, FL rt 2 h | 91:1 |
| 19 | DBI 1 mol/[NBu$_4$]Br$_3$ 0.1 mol/DCM, FL rt 3 h | 87:3 |
| 20 | DBI 1 mol/[NBu$_4$]Br$_3$ 0.05 mol/DCM, FL rt 2 h | 78:1 |
| 21 | DBI 1 mol/[NBu$_4$]Br$_3$ 0.05 mol/DCM, FL rt 3 h | 84:2 |
| 21 | DBI 1 mol/[NBu$_4$]Br$_3$ 0.05 mol/DCM, FL rt 4 h | 81:4 |

[a] All quantities in mole/mole of 4-chlorophenylacetic acid.

Example 12

Bromodecarboxylation of Alkanoic Acids

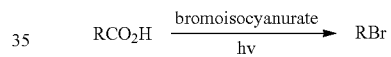

A mixture of alkanoic acid RCO$_2$H (2 mmol), bromoisocyanurate, additive (optionally) and solvent (12 mL) was stirred under fluorescent room light irradiation (FL). The reaction mixture washed with 1 M aq Na$_2$SO$_3$, dried over Na$_2$SO$_4$, filtered through short silica gel pad and concentrated in vacuo to yield crude alkyl bromide RBr. Optionally, the crude bromide was purified by chromatography on silica gel. The results are presented in Table 11.

TABLE 11

Bromodecarboxylation of alkanoic acids RCO$_2$H [a]

| entry | RCO$_2$H | Reaction conditions | yield, % RBr |
|---|---|---|---|
| 1 | H(CH$_2$)$_{11}$CO$_2$H | DBI 1 mol/Br$_2$ 0.3 mol/DCM, rt FL 4 h | 84 |
| 2 | H(CH$_2$)$_{11}$CO$_2$H | DBI 1 mol/[NBu$_4$]Br$_3$ 0.1 mol/ DCM, rt FL 5 h | 95[b] |
| 3 | c-C$_6$H$_{11}$(CH$_2$)$_2$CO$_2$H | DBI 1 mol/[NBu$_4$]Br$_3$ 0.3 mol/ DCM, rt FL 4 h | 89 |
| 4 | Br(CH$_2$)$_{10}$CO$_2$H | DBI 1 mol/Br$_2$ 0.3 mol/DCM, rt FL 4 h | 85 |
| 5 | MeO$_2$C(CH$_2$)$_6$CO$_2$H | DBI 1 mol/Br$_2$ 0.3 mol/DCM, rt FL 4 h | 83 |
| 6 | 4-ClC$_6$H$_4$CO(CH$_2$)$_2$CO$_2$H | DBI 1 mol/Br$_2$ 0.3 mol/DCM, rt FL 4 h | 99 |
| 7 | PhCO(CH$_2$)$_3$CO$_2$H | DBI 1 mol/[NBu$_4$]Br$_3$ 0.1 mol/ DCM, rt FL 5 h | 69 |
| 8 | PhCO(CH$_2$)$_4$CO$_2$H | DBI 1 mol/[NBu$_4$]Br$_3$ 0.3 mol/ DCM, rt FL 4 h | 84 |
| 9 | PhCH$_2$CO$_2$H | DBI 1 mol/[NBu$_4$]Br$_3$ 0.1 mol/ DCM, rt FL 2 h | 90 |

TABLE 11-continued

Bromodecarboxylation of alkanoic acids RCO$_2$H [a]

| entry | RCO$_2$H | Reaction conditions | yield, % RBr |
|---|---|---|---|
| 10 | 4-ClC$_6$H$_4$CH$_2$CO$_2$H | DBI 1 mol/[NBu$_4$]Br$_3$ 0.1 mol/ DCM, rt FL 2 h | 97 |
| 11 | 4-PhC$_6$H$_4$CH$_2$CO$_2$H | DBI 1 mol/[NBu$_4$]Br$_3$ 0.1 mol/ DCM, rt FL 2 h | 82 |
| 12 | PhCHMeCO$_2$H | DBI 1 mol/[NBu$_4$]Br$_3$ 0.5 mol/ DCM, rt FL 3 h | 87 |
| 13 | H(CH$_2$)$_4$CHMeCO$_2$H | DBI 1 mol/[NBu$_4$]Br$_3$ 0.5 mol/ DCM, rt FL 3 h | 97[b] |
| 14 | H(CH$_2$)$_{16}$CHMeCO$_2$H | DBI 1 mol/[NBu$_4$]Br$_3$ 0.5 mol/ DCM, rt FL 4 h | 92 |
| 15 | Et$_2$C(CO$_2$Et)CO$_2$H | DBI 1 mol/[NBu$_4$]Br$_3$ 0.5 mol/ DCM, rt FL 4 h | 85 |
| 16 | c-C$_4$H$_9$CO$_2$H | DBI 1 mol/[NBu$_4$]Br$_3$ 0.5 mol/ DCM, rt FL 3 h | 96[b] |
| 17 | c-C$_6$H$_{11}$CO$_2$H | DBI 1 mol/[NBu$_4$]Br$_3$ 0.5 mol/ DCM, rt FL 3 h | 80[b] |
| 18 | c-C$_5$H$_{11}$CH(CO$_2$H)$_2$ | DBI 2 mol/[NBu$_4$]Br$_3$ 1 mol/ DCM, rt FL 3 h | 25 (55[b]) |
| 19 | H(CH$_2$)$_{10}$CHBrCO$_2$H | DBI 1 mol/[NBu$_4$]Br$_3$ 0.5 mol/ DCM, rt FL 3 h | 60 |
| 20 | PhCHClCO$_2$H | DBI 1 mol/[NBu$_4$]Br$_3$ 0.5 mol/ DCM, rt FL 3 h | 80 |
| 21 | H(CH$_2$)$_6$CHClCO$_2$H | DBI 1 mol/[NBu$_4$]Br$_3$ 0.5 mol/ DCM, rt FL 3 h | 68 |
| 22 | EtO$_2$C(CH$_2$)$_4$CHClCO$_2$H | DBI 1 mol/[NBu$_4$]Br$_3$ 0.5 mol/ DCM, rt FL 3 h | 70 |
| 23 | PhCHFCO$_2$H | DBI 1 mol/[NBu$_4$]Br$_3$ 0.5 mol/ DCM, rt FL 3 h | 73 |
| 24 | H(CH$_2$)$_{12}$CHFCO$_2$H | DBI 1 mol/[NBu$_4$]Br$_3$ 0.5 mol/ DCM, rt FL 3 h | 76 |
| 25 | EtO$_2$C(CH$_2$)$_4$CHFCO$_2$H | DBI 1 mol/[NBu$_4$]Br$_3$ 0.5 mol/ DCM, rt FL 3 h | 64 |
| 26 | H(CH$_2$)$_4$CF(CO$_2$Et)CO$_2$H | DBI 1 mol/[NBu$_4$]Br$_3$ 0.5 mol/ DCM, rt FL 4 h | 73 |
| 27 | (steroid with HCOO, HCOO, HOOCH substituents, CO$_2$H side chain) | DBI 1 mol/[NBu$_4$]Br$_3$ 0.3 mol/ DCM, rt FL 4 h | 68 |
| 28 | phthalimide-N(CH$_2$)$_5$CO$_2$H | DBI 1 mol/Br$_2$ 0.3 mol/DCM, rt FL 4 h | 61 |
| 29 | spiro-bicyclobutane with CO$_2$H and CO$_2$Et | DBI 1 mol/[NBu$_4$]Br$_3$ 0.5 mol/ DCM, rt FL 4 h | 80 |
| 30 | MeO$_2$C—(cubane)—CO$_2$H | DBI 1 mol/[NBu$_4$]Br$_3$ 0.5 mol/ DCM, rt FL 2 h | 52 |
| 31 | cyclohexane with HO$_2$C and 4-ClC$_6$H$_4$CO-O substituents | DBI 1 mol/[NBu$_4$]Br$_3$ 0.5 mol/ DCM, rt FL 3 h | 60[c] |

TABLE 11-continued

Bromodecarboxylation of alkanoic acids $RCO_2H$ [a]

| entry | $RCO_2H$ | Reaction conditions | yield, % RBr |
|---|---|---|---|
| 32 | norbornane-CO₂H | DBI 1 mol/[NBu₄]Br₃ 0.5 mol/ DCM, rt FL 3 h | 90[d] |
| 33 | camphor-like bicyclic ketone-CO₂H | DBI 1 mol/[NBu₄]Br₃ 0.5 mol/ DCM, rt FL 4 h | 38 |
| 34 | adamantyl-CH₂-CO₂H | DBI 1 mol/[NBu₄]Br₃ 0.5 mol/ DCM, rt FL 4 h | 86 |
| 35 | 1-adamantyl-CO₂H | DBI 1 mol/[NBu₄]Br₃ 0.5 mol/ DCM, rt FL 4 h | 90 |
| 36 | 2-adamantyl-CO₂H | DBI 1 mol/[NBu₄]Br₃ 0.5 mol/ DCM, rt FL 4 h | 72 |
| 37 | Boc—N(azetidine)—CO₂H | DBI 1 mol/[NBu₄]Br₃ 0.5 mol/ DCM, rt FL 3 h | 26 |
| 38 | Boc—N(piperidine)—CH₂CO₂H | DBI 1 mol/[NBu₄]Br₃ 0.3 mol/ DCM, rt FL 4 h | 76 |
| 39 | Boc—N(piperidine)—CO₂H | DBI 1 mol/[NBu₄]Br₃ 0.5 mol/ DCM, rt FL 3 h | 26 |
| 40 | MeSO₂—N(piperidine)—CO₂H | DBI 1 mol/[NBu₄]Br₃ 0.5 mol/ DCM, rt FL 3 h | 82 |
| 41 | $CH_2BrCHBr(CH_2)_5CO_2H$ | DBI 1 mol/[NBu₄]Br₃ 0.5 mol/ DCM, rt FL 4 h | 77 |
| 42 | phthalimido-$N(CH_2)_5CHFCO_2H$ | DBI 1 mol/[NBu₄]Br₃ 0.5 mol/ DCM, rt FL 3 h | 67 |

[a] All quantities in mole/mole of alkanoic acid.
[b] Yield determined by GC.
[c] Mixture of 1.4:1 trans/cis bromides ($^1$H NMR)
[d] Mixture of 2:1 exo/endo bromides ($^1$H NMR)

Entry 1: 1-Bromoundecane $^1$H NMR: δ 3.38 (t, J=7 Hz, 2H), 1.84 (m, 2H), 1.40 (m, 2H), 1.27 (s, 14H), 0.87 (t, J=7 Hz, 3H) ppm; $^{13}$C NMR: δ 33.9, 33.0, 32.0, 29.71, 29.69, 29.59, 29.5, 28.9, 28.3, 22.8, 14.2 ppm.

Entry 3: (2-Bromoethyl)cyclohexane $^1$H NMR: δ 3.24 (t, J=7 Hz, 2H), 1.61-1.79 (m, 7H), 1.40-1.52 (m, 3H), 0.85-0.98 (m, 2H) ppm; $^{13}$C NMR: δ 40.4, 36.3, 32.7, 31.8, 26.5, 26.1 ppm.

Entry 4: 1,10-Dibromodecane $^1$H NMR: δ 3.39 (t, J=7 Hz, 4H), 1.84 (m, 4H), 1.41 (m, 4H), 1.29 (s, 8H) ppm; $^{13}$C NMR: δ 34.0, 32.8, 29.3, 28.7, 28.1 ppm.

Entry 5: Methyl 7-bromoheptanoate $^1$H NMR: δ 3.66 (s, 3H), 3.40 (t, J=7 Hz, 2H), 2.31 (t, J=7 Hz, 2H), 1.86 (m, 2H), 1.64 (m, 2H), 1.45 (m, 2H), 1.37 (m, 2H) ppm; $^{13}$C NMR: δ 173.9, 51.4, 33.8, 33.7, 32.5, 28.2, 27.7, 24.6 ppm.

Entry 6: 3-Bromo-1-(4-chlorophenyl)propan-1-one $^1$H NMR: δ 7.89 (d, J=9 Hz, 2H), 7.44 (d, J=9 Hz, 2H), 3.73 (t, J=7 Hz, 2H), 3.55 (t, J=7 Hz, 2H) ppm; $^{13}$C NMR: δ 195.7, 139.9, 134.5, 129.4, 129.0, 41.4, 25.6 ppm.

Entry 7: 4-Bromo-1-phenylbutan-1-one $^1$H NMR: δ 7.99 (d, J=4 Hz, 2H), 7.58 (t, J=7 Hz, 1H), 7.48 (t, J=8 Hz, 2H), 3.56 (t, J=6 Hz, 2H), 3.18 (t, J=7 Hz, 2H), 2.30 (quint, J=7 Hz, 2H) ppm; $^{13}$C NMR: δ 198.5, 136.6, 133.1, 128.5, 127.9, 36.4, 33.6, 26.8 ppm.

Entry 8: 5-Bromo-1-phenylpentan-1-one $^1$H NMR: δ 7.95 (d, J=7 Hz, 2H), 7.56 (t, J=7 Hz, 1H), 7.46 (t, J=7 Hz, 2H), 3.45 (t, J=7 Hz, 2H), 3.01 (t, J=7 Hz, 2H), 1.87-2.0 (m, 4H) ppm; $^{13}$C NMR: δ 199.7, 136.9, 133.2, 128.7, 128.1, 37.5, 33.4, 32.3, 22.9 ppm.

Entry 9: Benzyl bromide $^1$H NMR: δ 7.46-7.59 (m, 5H), 4.45 (s, 2H) ppm; $^{13}$C NMR δ 137.7, 128.9, 128.6, 128.3, 33.6 ppm.

Entry 10: 4-Chlorobenzyl bromide $^1$H NMR: δ 7.33 (s, 4H), 4.47 (s, 2H) ppm; $^{13}$C NMR: δ 136.3, 134.3, 130.4, 129.0, 32.5 ppm.

Entry 11: 4-Bromomethylbiphenyl $^1$H NMR: δ 7.54-7.61 (m, 4H), 7.41-7.48 (m, 4H), 7.34-7.39 (m, 1H), 4.52 (s, 2H) ppm; $^{13}$C NMR: δ 141.3, 140.4, 136.8, 129.5, 128.8, 127.6, 127.5, 127.1, 33.5 ppm.

Entry 12: (1-Bromoethyl)benzene $^1$H NMR: δ 7.27-7.46 (m, 5H), 5.22 (q, J=7 Hz, 1H), 2.05 (d, J=7 Hz, 3H) ppm; $^{13}$C NMR: δ 143.3, 128.7, 128.4, 126.9, 49.6, 26.9 ppm.

Entry 14: 2-Bromooctadecane $^1$H NMR: δ 4.12 (m, 1H), 1.75-1.89 (m, 2H), 1.71 (d, J=7 Hz, 2H), 1.40-1.58 (m, 3H), 1.28 (m, 26H), 0.9 (t, J=7 Hz, 3H) ppm; $^{13}$C NMR: δ 51.5, 41.4, 32.1, 29.88, 29.85, 29.82, 29.76, 29.67, 29.55, 29.2, 27.9, 26.6, 22.8, 14.2 ppm.

Entry 15: Ethyl 2-bromo-2-ethylbutyrate $^1$H NMR: 4.21 (q, J=7 Hz, 2H), 2.09 (m, 4H), 1.27 (t, J=7 Hz, 3H), 0.95 (t, J=7 Hz, 6H) ppm; $^{13}$C NMR 170.9, 70.1, 62.0, 32.7, 14.1, 10.1 ppm.

Entry 18: (Dibromomethyl)cyclopentane $^1$H NMR: δ 5.70 (d, J=6 Hz, 2H), 2.60-2.77 (m, 1H), 1.86-1.96 (m, 2H), 1.40-1.78 (6H) ppm; $^{13}$C NMR: δ 52.6, 52.5, 31.6, 26.0 ppm.

Entry 19: 1,1-Dibromoundecane $^1$H NMR: δ 5.7 (t, J=6 Hz, 1H), 2.39 (m, 2H), 1.48-1.58 (m, 2H), 1.27 (m, 14H), 0.88 (t, J=7 Hz, 3H) ppm; $^{13}$C NMR: δ 46.4, 45.6, 32.0, 29.7, 29.6, 29.5, 29.5, 28.4, 28.2, 22.8, 14.2 ppm.

Entry 20: (Bromochloromethyl)benzene $^1$H NMR: δ 7.56-7.63 (m, 2H), 7.33-7.45 (m, 3H), 6.76 (s, 1H) ppm; $^{13}$C NMR: δ 141.3, 130.0, 128.8, 126.3, 57.6 ppm.

Entry 21: 1-Bromo-1-chloroheptane $^1$H NMR: δ 5.76 (t, 1H, J=6 Hz, 1H), 2.28 (m, 2H), 1.53 (m, 2H), 1.3 (m, 7H), 0.89 (t, J=7 Hz, 3H) ppm; $^{13}$C NMR: δ 61.1, 44.8, 31.2, 28.2, 27.1, 22.6, 14.1 ppm.

Entry 22: Ethyl 6-bromo-6-chlorohexanoate $^1$H NMR: 5.75 (t, J=6 Hz, 1H), 4.09 (q, J=7 Hz, 2H), 2.24-2.33 (m, 4H), 1.60-1.70 (m, 2H), 1.51-1.60 (m, 2H), 1.20 (t, J=7 Hz, 3H) ppm; $^{13}$C NMR 173.2, 60.5, 60.4, 53.5, 44.2, 34.0, 26.5, 23.8, 14.3 ppm.

Entry 23: (Bromofluoromethyl)benzene $^1$H NMR: δ 7.33-7.55 (m, 6H) ppm; 13C NMR: δ 138.8 (d, $J_{CF}$=20 Hz), 130.3, 128.8, 125.2 (d, $J_{CF}$=6 Hz), 92.2 (d, $J_{CF}$=254 Hz) ppm; $^{19}$F NMR: δ −133.3 ppm.

Entry 24: 1-Bromo-1-fluorotridecane $^1$H NMR: δ 6.45 (dt, J=51, 5 Hz, 1H), 2.07-2.29 (m, 2H), 1.46-1.56 (m, 2H), 1.27 (m, 19H), 0.88 (t, J=7 Hz, 3H) ppm; 95.9 (d, $J_{CF}$=252 Hz), 40.8 (d, $J_{CF}$=19 Hz), 32.0, 29.79, 29.78, 29.73, 29.6, 29.5, 28.8, 25.22, 25.18, 22.8, 14.1 ppm; $^{19}$F NMR: −133.3 ppm.

Entry 25: Ethyl 6-bromo-6-fluorohexanoate $^1$H NMR: 6.42 (dt, J=50, 5.4 Hz, 1H), 4.10 (q, J=7 Hz, 2H), 2.28 (t, J=7 Hz, 2H), 2.00-2.23 (m, 2H), 1.60-1.69 (m, 2H), 1.56-1.60 (m, 2H), 1.20 (t, J=7 Hz, 3H) ppm; $^{13}$C NMR 173.2, 95.2 (d, $J_{CF}$=252 Hz), 60.4, 40.2 (d, $J_{CF}$=19 Hz), 34.0, 24.6 (d, $J_{CF}$=4 Hz), 24.0, 14.3 ppm; $^{19}$F NMR: δ −134.0 ppm.

Entry 26: Ethyl 2-bromo-2-fluorohexanoate $^1$H NMR: 4.34 (q, J=7 Hz, 2H), 2.30-2.50 (m, 2H), 1.50-1.65 (2H), 1.31-1.45 (m, 6H), 0.93 (t, J=7 Hz, 3H) ppm; $^{13}$C NMR 166.3 (d, $J_{CF}$=27 Hz), 98.7 (d, $J_{CF}$=266 Hz), 63.1, 41.4, (d, $J_{CF}$=21 Hz), 26.4 (d, $J_{CF}$=1.4 Hz), 22.1, 13.9, 13.8 ppm; $^{19}$F NMR: δ −120.1 ppm.

Entry 27: 3α, 7α, 12α-Triformyloxy-5β-23-bromo-24-nor-cholane $^1$H NMR: δ 8.15 (s, 1H), 8.02 (s, 1H), 8.01 (s, 1H), 5.27 (m, 1H), 5.07 (m, 1H), 4.70 (m, 1H), 3.43-3.35 (m, 1H), 3.27-3.38 (m, 1H), 1.02-2.18 (m, 25H), 0.94 (s, 3H), 0.85 (d, J=6 Hz, 3H), 0.77 (s, 3H) ppm; $^{13}$C NMR: δ 160.69, 160.68, 160.6, 75.4, 73.9, 70.8, 47.5, 45.3, 43.1, 40.9, 39.0, 37.8, 34.6, 34.6, 34.5, 34.4, 34.4, 31.8, 31.5, 28.7, 27.4, 26.7, 25.7, 22.9 ppm.

Entry 28: N-(5-Bromopentyl)phthalimide $^1$H NMR: δ 7.80 (dd, J=5, 3 Hz, 2H), 7.70 (dd, J=5, 3 Hz, 2H), 3.68 (t, J=7 Hz, 2H), 3.38 (t, J=7 Hz, 2H), 1.89 (m, 2H), 1.70 (m, 2H), 1.49 (m, 2H) ppm; $^{13}$C NMR: δ 168.3, 133.9, 132.0, 37.6, 33.4, 32.2, 27.7, 25.3 ppm.

Entry 29: Ethyl 1-bromocyclobutanoate $^1$H NMR: δ 4.19 (q, J=7 Hz, 2H), 2.80-2.90 (m, 2H), 2.50-2.60 (m, 2H), 2.10-2.20 (m, 1H), 1.76-1.87 (m, 1H), 1.25 (t, J=7 Hz, 3H) ppm; $^{13}$C NMR: δ 171.5, 61.9, 54.3, 37.2, 16.7, 13.9 ppm.

Entry 30: Methyl 4-bromocubanecarboxylate $^1$H NMR: δ 4.22-4.35 (m, 6H), 3.70 (s, 3H) ppm; $^{13}$C NMR: δ 172.0, 63.3, 56.4, 54.7, 51.8, 47.9 ppm.

Entry 31: trans-1-Bromo-2-(4-chlorobenzoyl)cyclohexane $^1$H NMR: δ 7.93 (d, J=9 Hz, 2H), 7.46 (d, J=9 Hz, 2H), 4.41 (m, 1H), 3.76 (m, 1H), 2.49 (m, 1H), 1.91-2.00 (m, 2H), 1.79-1.89 (m, 2H), 1.37-1.50 (m, 3H) ppm; $^{13}$C NMR: δ 200.0, 140.0, 134.7, 130.0, 129.2, 54.1, 51.4, 37.5, 31.9, 27.0, 24.9 ppm.

Entry 32: endo-2-Bromonorbornane $^1$H NMR: δ 4.27-4.33 (m, 1H) ppm; $^{13}$C NMR: δ 54.1, 43.5, 41.6, 37.7, 37.17, 29.6, 24.5 ppm.

Entry 32: exo-2-Bromonorbornane $^1$H NMR: δ 3.96-4.02 (m, 1H) ppm; $^{13}$C NMR: δ 54.1, 46.6, 44.0, 37.2, 35.6, 28.2, 27.7 ppm.

Entry 33: (1S)-1-Bromoapocamphan-2-one $^1$H NMR: δ 2.52 (m, 1H), 1.93-2.27 (m, 5H), 1.50 (m, 1H), 1.08 (s, 3H), 0.95 (s, 3H) ppm; $^{13}$C NMR: δ 209.0, 77.1, 49.1, 42.5, 40.7, 32.8, 28.1, 20.1, 19.6 ppm.

Entry 34: 1-(Bromomethyl)adamantine $^1$H NMR: δ 3.13 (s, 2H), 1.98 (m, 3H), 1.69 (d, J=12 Hz, 3H), 1.62 (d, J=12 Hz, 3H), 1.54 (m, 6H) ppm; $^{13}$C NMR: δ 48.4, 40.7, 36.8, 33.6, 28.5 ppm.

Entry 35: 1-Bromoadamantane $^1$H NMR: δ 2.37 (d, J=3 Hz, 6H), 2.1 (m, 3H), 1.73 (m, 6H) ppm; $^{13}$C NMR: δ 49.4, 35.6, 32.6 ppm.

Entry 36: 3-Bromonoradamantane $^1$H NMR: δ 2.65 (t, J=7 Hz, 1H), 2.16-2.30 (m, 6H), 1.95-2.05 (m, 2H), 1.43-1.63 (m, 4H) ppm; $^{13}$C NMR: δ 66.1, 55.4, 48.8, 43.4, 38.5, 33.4 ppm.

Entry 37: 1-Boc-3-bromoazetidine $^1$H NMR: δ 4.49 (m, 3H), 4.16 (m, 2H), 1.42 (s, 9H) ppm; $^{13}$C NMR: δ 155.8, 80.3, 60.3, 33.0, 28.4 ppm.

Entry 38: 1-Boc-4-(bromomethyl)piperidine $^1$H NMR: δ 4.13 (m, 1H), 3.29 (d, J=6 Hz, 2H), 2.69 (m, 2H), 1.78-1.85 (m, 3H), 1.46 (s, 9H), 1.10-1.23 (m, 2H) ppm; $^{13}$C NMR: δ 154.8, 79.5, 43.6, 38.9, 38.7, 30.9, 28.5 ppm.

Entry 39: 1-Boc-4-bromopiperidine $^1$H NMR: δ 4.30 (m, 1H), 3.60-3.70 (m, 2H), 3.24-3.32 (m, 2H), 2.00-2.10 (m, 2H), 1.85-1.95 (m, 2H), 1.43 (s, 9H) ppm; $^{13}$C NMR: δ 154.7, 79.9, 49.6, 42.2 (bs), 35.7, 28.5 ppm.

Entry 40: 4-Bromo-1-(methylsulfonyl)piperidine $^1$H NMR: δ 4.43 (m, 1H), 3.37 (m, 4H), 2.80 (s, 3H), 2.16-2.28 (m, 2H), 2.05-2.14 (m, 2H) ppm; $^{13}$C NMR: δ 48.2, 43.2, 35.0, 34.7 ppm.

Entry 41: 1,2,7-Tribromoheptane $^1$H NMR: δ 4.17 (m, 1H), 3.86 (dd, J=10, 4 Hz, 1H), 3.62 (t, J=10 Hz, 1H), 3.42 (t, J=7 Hz, 1H), 2.11-2.21 (m, 1H), 1.75-1.94 (m, 3H), 1.41-1.67 (m, 5H) ppm; $^{13}$C: δ 52.8, 36.3, 35.9, 33.7, 32.6, 27.5, 26.1 ppm.

Entry 42: N-(6-Bromo-6-fluorohexyl)phthalimide $^1$H NMR: δ 7.83-7.86 (m, 2H), 7.70-7.73 (m, 2H), 6.44 (dt, J=50, 5 Hz, 1H), 3.70 (t, 2H), 2.08-2.28 (m, 2H), 1.71 (m, 2H), 1.51-1.61 (m, 3H), 1.36-1.46 (m, 2H) ppm; $^{13}$C NMR: δ 168.4, 133.9, 132.1, 123.1, 95.4 (d, $J_{CF}$=252 Hz), 40.7 (d, $J_{CF}$=41 Hz), 37.7, 28.3, 25.9, 24.6, 24.56 ppm; $^{19}$F NMR: δ −133.8 ppm.

Example 13

Bromodecarboxylation of Lauric Acid: Solvent Selection

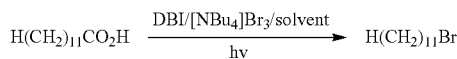

A mixture of lauric acid (0.5 mmol), DBI (0.5 mmol), [NBu$_4$]Br$_3$ (0.15 mmol), and solvent (4 mL) was stirred under fluorescent room light irradiation (FL) or warm-white 3 W LED lamp irradiation (LL). An aliquot of the reaction mixture washed with 1 M aq Na$_2$SO$_3$, dried over Na$_2$SO$_4$, and filtered through short neutral silica gel pad. The yield of 1-bromoundecane was determined by gas chromatography (GC) using 1,2,4,5-tetrachlorobenzene as internal standard. The results are presented in Table 12.

TABLE 12

Bromodecarboxylation of lauric acid $^a$

| entry | Reaction conditions | yield, % $^b$ |
|---|---|---|
| 1 | DBI 1 mol/[NBu$_4$]Br$_3$ 0.3 mol/DCM, rt FL 4 h | 98 |
| 2 | DBI 1 mol/[NBu$_4$]Br$_3$ 0.3 mol/DCE, rt FL 4 h | 55 |
| 3 | DBI 1 mol/[NBu$_4$]Br$_3$ 0.3 mol/CHCl$_3$, rt FL 4 h | 73 |
| 4 | DBI 1 mol/[NBu$_4$]Br$_3$ 0.3 mol/CCl$_4$, rt FL 4 h | 6 |
| 5 | DBI 1 mol/Br$_2$ 1 mol/DCM, rt FL 1 h | 43 |
| 6 | DBI 1 mol/Br$_2$ 1 mol/DCM, rt FL 2 h | 73 |
| 7 | DBI 1 mol/Br$_2$ 1 mol/DCM, rt FL 3 h | 70 |
| 8 | DBI 1 mol/Br$_2$ 1 mol/DCM, rt FL 4 h | 60 |
| 9 | DBI 1 mol/Br$_2$ 1 mol/CCl$_4$, rt FL 1 h | 11 |
| 10 | DBI 1 mol/Br$_2$ 1 mol/CCl$_4$, rt FL 2 h | 27 |
| 11 | DBI 1 mol/Br$_2$ 1 mol/CCl$_4$, rt FL 18 h | 20 |
| 12 | DBI 1 mol/[NBu$_4$]Br$_3$ 0.3 mol/C$_6$H$_6$, rt FL 4 h | 77 |
| 13 | DBI 1 mol/[NBu$_4$]Br$_3$ 0.3 mol/PhCl, rt FL 4 h | 73 |
| 14 | DBI 1 mol/[NBu$_4$]Br$_3$ 0.3 mol/MeCN, rt FL 4 h | 29 |
| 15 | DBI 1 mol/[NBu$_4$]Br$_3$ 0.3 mol/MeOAc, rt LL 1 h | 44 |
| 16 | DBI 1 mol/[NBu$_4$]Br$_3$ 0.3 mol/MeOAc, rt LL 2 h | 53 |
| 17 | DBI 1 mol/[NBu$_4$]Br$_3$ 0.3 mol/MeOAc, rt LL 3 h | 53 |
| 18 | DBI 1 mol/[NBu$_4$]Br$_3$ 0.3 mol/EtOAc, rt LL 1 h | 60 |
| 19 | DBI 1 mol/[NBu$_4$]Br$_3$ 0.3 mol/EtOAc, rt LL 2 h | 68 |
| 20 | DBI 1 mol/[NBu$_4$]Br$_3$ 0.3 mol/EtOAc, rt LL 4 h | 68 |

$^a$ All quantities in mole/mole of lauric acid.
$^b$ 1-Bromoundecane analyzed by GC.

Example 14

Bromodecarboxylation of Lauric Acid: N-Bromoamide Selection

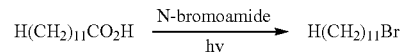

A mixture of lauric acid (0.5 mmol), N-bromoamide (0.5 mmol), [NBu$_4$]Br$_3$ (0.15 mmol), and DCM (4 mL) was stirred under fluorescent room light irradiation (FL) or warm-white 3 W LED lamp irradiation (LL). An aliquot of the reaction mixture washed with 1 M aq Na$_2$SO$_3$, dried over Na$_2$SO$_4$, and filtered through short neutral silica gel pad. The yield of 1-bromoundecane was determined by gas chromatography (GC) using 1,2,4,5-tetrachlorobenzene as internal standard. The results are presented in Table 13.

TABLE 13

N-Bromoamides as reagents for radical bromodecarboxylation $^a$

| entry | Reaction conditions | yield, % $^b$ |
|---|---|---|
| | DBI 1 mol/[NBu$_4$]Br$_3$ 0.3 mol/DCM, rt FL 4 h | 98 |
| | DBI 1 mol/[NBu$_4$]Br$_3$ 0.3 mol/DCM, rt FL 20 h | 71 |
| | NBS 1 mol/[NBu$_4$]Br$_3$ 0.3 mol/DCM, rt FL 4 h | 1 |
| | NBS 1 mol/[NBu$_4$]Br$_3$ 0.3 mol/DCM, rt FL 20 h | 2 |
| | NBSsac 1 mol/[NBu$_4$]Br$_3$ 0.3 mol/DCM, rt FL 4 h | 1 |
| | DBDMH 1 mol/[NBu$_4$]Br$_3$ 0.3 mol/DCM, rt FL 4 h | 4 |
| | DBDMH 1 mol/[NBu$_4$]Br$_3$ 0.3 mol/DCM, rt FL 20 h | 10 |
| | BTH 1 mol/[NBu$_4$]Br$_3$ 0.3 mol/DCM, rt FL 4 h | 2 |
| | BTH 1 mol/[NBu$_4$]Br$_3$ 0.3 mol/DCM, rt FL 20 h | 5 |

$^a$ All quantities in mole/mole of lauric acid.
$^b$ 1-Bromoundecane analyzed by GC.

Example 15

Bromodecarboxylation of Lauric Acid: Recovery of Onium Compound

A mixture of lauric acid (3.13 g, 15.7 mmol), dibromoisocyanuric acid DBI (4.50 g, 15.7 mmol), tetrapropylammonium tribromide [NPr$_4$]Br$_3$ (2.00 g, 4.7 mmol) and DCM (45 mL) was stirred under warm-white 3 W LED lamp irradiation (LL) for 7 h at 0° C. The mixture was filtered and the filtrate was washed with 1M aq Na$_2$SO$_3$ (6.3 mL, 6.3 mmol) and water (20 mL), dried over Na$_2$SO$_4$, filtered and concentrated in vacuo to give 1-bromoundecane (3.56 g, 97% yield).

The combined aqueous phases were treated with Br$_2$ (1.01 g, 6.3 mmol), washed with DCM (2×60 mL). DCM fraction was dried over Na$_2$SO$_4$, filtered and concentrated in vacuo giving g (1.36 g, 68% recovery) of [NPr$_4$]Br$_3$.

Example 16

Bromodecarboxylation of Lauric Acid with Bromoisocyanurate

A: Preparation of Bromoisocyanurate

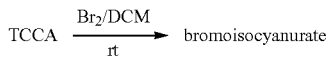

The mixture of trichloroisocyanuric acid TCCA (10.0 g, 43.1 mmol), $Br_2$ (41.9 g, 262 mmol) and DCM (50 mL) was stirred at rt in the dark for 18 h. The precipitate was filtered off, washed on the filter with DCM and treated with $Br_2$ (41.9 g, 262 mmol) in DCM (50 mL) at rt in the dark for 18 h. The precipitate was filtered off, washed on the filter with DCM and dried in vacuo giving 14.1 g of bromoisocyanurate.

B: Bromodecarboxylation of Lauric Acid with Bromoisocyanurate

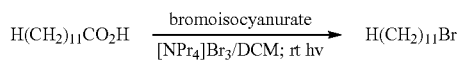

A mixture of lauric acid (0.28 g, 1.4 mmol), bromoisocyanurate from step A (0.39 g), tetrapropylammonium tribromide $[NPr_4]Br_3$ (0.58 g, 1.4 mmol), and DCM (4 mL) was stirred at 0° C. under 3 W warm-white LED lamp irradiation (LL) for 5 h. The mixture was washed with 1 M aq $Na_2SO_3$, dried over $Na_2SO_4$, filtered and concentrated in vacuo. The residue was purified by chromatography on silica to yield 0.30 g (90%) of 1-bromoundecane.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A process for the preparation of organic bromide of formula (1A) from a carboxylic acid of formula (2A) represented by scheme 1:

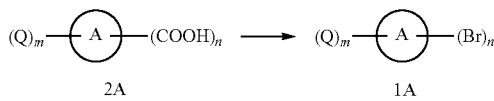

said process comprises radical bromodecarboxylation reaction of carboxylic acid (2A) with a bromoisocyanurate to yield organic bromide (1A);
wherein
said bromoisocyanurate is tribromoisocyanuric acid, dibromoisocyanuric acid, bromodichloroisocyanuric acid, dibromochloroisocyanuric acid, bromochloroisocyanuric acid, or any combination thereof;
A is arene, alkane, cycloalkane or saturated heterocycle;
n is an integer of at least 1;
m is an integer of at least 0; and
each Q is independently F, Cl, Br, $R^1$, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;
wherein each $R^1$ is independently aryl, alkyl, cycloalkyl or heterocyclyl, wherein said $R^1$ is optionally substituted by one or more substituents of $R^2$;
wherein each $R^2$ is independently F, Cl, Br, COOH, acyl, aryl, alkyl, cycloalkyl or heterocyclyl;
wherein if either one of $R^2$ in (2A) is carboxylic group COOH, then the respective $R^2$ in (1A) is Br;
wherein the position of said Br and Q in said structure of formula (1A) correspond to the same position of said COOH and Q, respectively in said structure of formula (2A).

2. The process of claim 1, wherein A is benzene.

3. The process of claim 1, wherein said organic bromide is bromoarene of formula (1B):

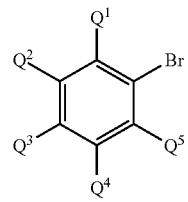

and said carboxylic acid is arenecarboxylic acid of formula (2B)

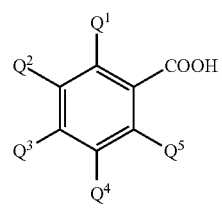

wherein $Q^1$, $Q^2$, $Q^3$, $Q^4$, and $Q^5$, are each independently selected from: H, F, Cl, Br, $R^1$, COOH, acyl, $C(O)R^1$, acetyl, benzoyl, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^2$, $N(R^1)SO_2R^1$, $N(acyl)_2$, $N[C(O)R^1]SO_2R^1$, $N[C(O)R^1]_2$, $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;
wherein each $R^1$ is independently aryl, alkyl, cycloalkyl or heterocyclyl; wherein $R^1$ is optionally substituted by one or more substituents of $R^2$;
wherein each $R^2$ is independently F, Cl, Br, COOH, acyl, aryl, alkyl, cycloalkyl or heterocyclyl;
wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Br.

4. The process of claim 3, wherein at least one of $Q^1$, $Q^2$, $Q^3$, $Q^4$, and/or $Q^5$ is F, Cl, Br, $CF_3$, $CCl_3$, CN, COOH, C(O)OMe, $NO_2$, $OCF_3$, and/or any two of $Q^1$ and $Q^2$, $Q^2$ and $Q^3$, $Q^3$ and $Q^4$, or $Q^4$ and $Q^5$, are joined to form a dihydrofuran-2,5-dione or pyrrolidine-2,5-dione ring.

5. The process of claim 1, wherein the molar ratio of bromoisocyanurate/(each carboxylic group of the carboxylic acid of formula (2A)) is between 0.1 and 2.

6. The process of claim 1, wherein said bromodecarboxylation reaction further comprises an additive.

7. The process of claim 6, wherein said additive is $Br_2$ (bromine), a salt comprising bromide or polybromide anion and organic or inorganic cation; or any combination thereof.

8. The process of claim 7, wherein said polybromide anion is an ion of formula

where p is an integer of at least 3 and q is an integer of at least 1 and not more than p/2.

9. The process of claim 7, wherein said cation is substituted or unsubstituted onium ion.

10. The process of claim 9, wherein said onium ion comprises substituted or unsubstituted ammonium, oxonium, phosphonium, sulfonium, arsonium, selenonium, telluronium, iodonium ion or any combination thereof.

11. The process of claim 10, wherein said ammonium ion is tertiary or quaternary ammonium, substituted or unsubstituted pyridinium, amidinium or guanidinium ion; or any combination thereof; or
said phosphonium ion is quaternary phosphonium ion; or
said sulfonium ion is tertiary sulfonium, substituted; or unsubstituted sulfoxonium, thiopyrylium or thiuronium ion; or any combination thereof; or
said oxonium ion is tertiary oxonium, substituted or unsubstituted pyrylium ion; or any combination thereof.

12. The process of claim 6, wherein the molar ratio of the additive/(each carboxylic group of the carboxylic acid of formula (2A)) is between 0.1 and 4.

13. The process of claim 1, wherein said bromodecarboxylation reaction further comprises an organic or inorganic solvent or combination thereof.

14. The process of claim 13, wherein said organic solvent is $CH_3CN$, $CH_3NO_2$, ester, a hydrocarbon solvent, or halocarbon solvent or combination thereof.

15. The process of claim 14, wherein said hydrocarbon solvent is $C_6H_6$; and said halocarbon solvent is $CH_2Cl_2$, $Cl(CH_2)_2Cl$, $CHCl_3$, $CCl_4$, $C_6H_5Cl$, o-$C_6H_4Cl_2$, $BrCCl_3$, $CH_2Br_2$, $CFCl_3$, $CF_3CCl_3$, $ClCF_2CFCl_2$, $BrCF_2CFClBr$, $CF_3CClBr_2$, $CF_3CHBrCl$, $C_6H_5F$, $C_6H_5CF_3$, 4-$ClC_6H_4CF_3$, 2,4-$Cl_2C_6H_3CF_3$, or any combination thereof.

16. The process of claim 1, wherein in order to accelerate the radical bromodecarboxylation reaction the reaction mixture is subjected to electromagnetic irradiation.

17. The process of claim 1, wherein said bromodecarboxylation reaction further comprises a radical initiator.

18. The process of claim 17, wherein said radical initiator is an azo compound or organic peroxide.

19. The process of claim 18, wherein said azo compound is azobisisobutyronitrile (AIBN) or 1,1'-azobis(cyclohexanecarbonitrile) (ABCN).

20. The process of claim 18, wherein said organic peroxide is benzoyl peroxide.

21. A radiation-sensitive composition comprising carboxylic acid of formula (2A)

and bromoisocyanurate which generates organic bromide of formula (1A)

upon electromagnetic irradiation,
wherein
the bromoisocyanurate is tribromoisocyanuric acid, dibromoisocyanuric acid, bromodichloroisocyanuric acid, dibromochloroisocyanuric acid, bromochloroisocyanuric acid, or any combination thereof;

A is arene, alkane, cycloalkane or saturated heterocycle;
n is an integer of at least 1;
m is an integer of at least 0;
each Q is independently F, Cl, Br, $R^1$, acyl, $C(O)R^1$, $C(O)OR^1$, C(O)OMe, C(O)Cl, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^1$, $N(R^1)SO_2R^1$, $N(acyl)_2$, $N[C(O)R^1]SO_2R^1$, $N[C(O)R^1]_2$, $CF_3$; or any two vicinal Q substituents are joined to form a 5- or 6-membered substituted or unsubstituted, saturated or unsaturated carbocyclic or heterocyclic ring;
wherein each $R^1$ is independently aryl, alkyl, cycloalkyl or heterocyclyl, wherein $R^1$ is optionally substituted by one or more substituents of $R^2$;
wherein each $R^2$ is independently F, Cl, Br, COOH, acyl, aryl, alkyl, cycloalkyl or heterocyclyl;
wherein if either one of $R^2$ in (2A) is a carboxylic group COOH, then the respective $R^2$ in (1A) is Br;
wherein the position of said Br and Q in said structure of formula (1A) correspond to the same position of said COOH and Q, respectively in said structure of formula (2A).

22. The composition of claim 21, wherein A is benzene.

23. The composition of claim 21, wherein said carboxylic acid is arenecarboxylic acid of formula (2B)

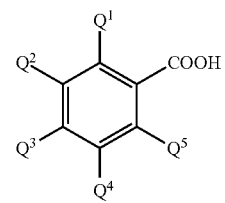

and said organic bromide is bromoarene of formula (1B)

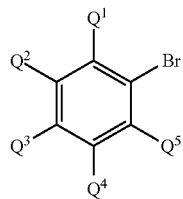

wherein $Q^1$, $Q^2$, $Q^3$, $Q^4$, and $Q^5$, are each independently selected from: H, F, Cl, Br, $R^1$, COOH, acyl, $C(O)R^1$, $C(O)OR^1$, $C(O)Cl$, $C(O)N(R^1)_2$, CN, $SO_2R^1$, $SO_3R^1$, $NO_2$, $N(R^1)_3^+$, $OR^1$, $OCF_3$, O-acyl, $OC(O)R^1$, $OSO_2R^1$, $SR^1$, S-acyl, $SC(O)R^1$, $N(R^1)$acyl, $N(R^1)C(O)R^2$, $N(R^1)SO_2R^1$, $N(acyl)_2$, $N[C(O)R^1]SO_2R^1$, $N[C(O)R^1]_2$, $CF_3$; or any two of $Q^1$ and $Q^2$, $Q^2$ and $Q^3$, $Q^3$ and $Q^4$, or $Q^4$ and $Q^5$, are joined to form a 5- or 6-membered substituted or unsubstituted, saturated or unsaturated carbocyclic or heterocyclic ring;
wherein each $R^1$ is independently aryl, alkyl, cycloalkyl or heterocyclyl wherein $R^1$ is optionally substituted by one or more substituents of $R^2$;
wherein each $R^2$ is independently F, Cl, Br, COOH, acyl, aryl, alkyl, cycloalkyl or heterocyclyl;
wherein if either one of $Q^1$, $Q^2$, $Q^3$, $Q^4$, $Q^5$, and/or $R^2$ in (2B) is carboxylic group COOH, then the respective $Q^1$, $Q^2$, $Q^3$, $Q^4$, $Q^5$, and/or $R^2$ in (1B) is Br.

24. The composition of claim 23, wherein at least one of $Q^2$, $Q^3$, Q, $Q^4$, and/or $Q^5$ is F, Cl, Br, $CF_3$, $CCl_3$, CN, COOH, $C(O)OMe$, $NO_2$, $OCF_3$, and/or any two of $Q^1$ and $Q^2$, $Q^2$ and $Q^3$, $Q^3$ and $Q^4$, or $Q^4$ and $Q^5$, are joined to form a dihydrofuran-2,5-dione or pyrrolidine-2,5-dione ring.

25. The composition of claim 21, wherein the molar ratio of bromoisocyanurate/(each carboxylic group of the carboxylic acid of formula (2A)) is between 0.1 and 2.

26. The composition of claim 21, which further comprises an additive.

27. The composition of claim 26, wherein said additive is $Br_2$ (bromine), a salt containing bromide or polybromide anion and organic or inorganic cation; or any combination thereof.

28. The composition of claim 27, wherein said polybromide anion is an ion of formula $$[Br_p]^{q-}$$

where p is an integer of at least 3 and q is an integer of at least 1 and no more than p/2.

29. The composition of claim 27, wherein said cation is substituted or unsubstituted onium ion.

30. The composition of claim 29, wherein said onium ion comprises substituted or unsubstituted ammonium, oxonium, phosphonium, sulfonium, arsonium, selenonium, telluronium, iodonium ion or any combination thereof.

31. The composition of claim 30, wherein said ammonium ion is tertiary or quaternary ammonium, substituted or unsubstituted pyridinium, amidinium or guanidinium ion; or any combination thereof; or wherein said phosphonium ion is quaternary phosphonium ion; or wherein said sulfonium ion is tertiary sulfonium, substituted or unsubstituted sulfoxonium, thiopyrylium or thiuronium ion; or any combination thereof; or wherein said oxonium ion is tertiary oxonium, substituted or unsubstituted pyrylium ion.

32. The composition of claim 31, wherein said quaternary ammonium is tetraalkylammonium, trialkylarylammonium, or trialkylbenzylammonium.

33. The composition of claim 26, wherein the molar ratio of the additive/(each carboxylic group of the carboxylic acid of formula (2A)) is between 0.1 and 4.

34. The composition of claim 21, which further comprises of an organic or inorganic solvent or combination thereof.

35. The composition of claim 34, wherein said organic solvent is $CH_3CN$, $CH_3NO_2$, ester, a hydrocarbon solvent, or halocarbon solvent or combination thereof.

36. The composition of claim 35, wherein said hydrocarbon solvent is $C_6H_6$; and said halocarbon solvent is $CH_2Cl_2$, $Cl(CH_2)_2Cl$, $CHCl_3$, $CCl_4$, $C_6H_5Cl$, o-$C_6H_4Cl_2$, $BrCCl_3$, $CH_2Br_2$, $CFCl_3$, $CF_3CCl_3$, $ClCF_2CFCl_2$, $BrCF_2CFClBr$, $CF_3CClBr_2$, $CF_3CHBrCl$, $C_6H_5F$, $C_6H_5CF_3$, 4-$ClC_6H_4CF_3$, 2,4-$Cl_2C_6H_3CF_3$, or any combination thereof.

* * * * *